US011543681B2

(12) United States Patent
Neitz et al.

(10) Patent No.: US 11,543,681 B2
(45) Date of Patent: Jan. 3, 2023

(54) OPHTHALMIC LENSES FOR TREATING MYOPIA

(71) Applicant: UNIVERSITY OF WASHINGTON, Seattle, WA (US)

(72) Inventors: Jay Neitz, Seattle, WA (US); James Kuchenbecker, Seattle, WA (US); Maureen Neitz, Seattle, WA (US)

(73) Assignee: University of Washington, Seattle, WA (US)

( * ) Notice: Subject to any disclaimer, the term of this patent is extended or adjusted under 35 U.S.C. 154(b) by 251 days.

(21) Appl. No.: 16/738,621

(22) Filed: Jan. 9, 2020

(65) Prior Publication Data

US 2020/0271955 A1    Aug. 27, 2020

Related U.S. Application Data

(63) Continuation of application No. 16/143,707, filed on Sep. 27, 2018, now Pat. No. 10,571,717, which is a
(Continued)

(51) Int. Cl.
*G02C 7/02* (2006.01)
*G02C 7/04* (2006.01)
(Continued)

(52) U.S. Cl.
CPC ........ *G02C 7/022* (2013.01); *B29D 11/00336* (2013.01); *G02C 7/02* (2013.01);
(Continued)

(58) Field of Classification Search
CPC .......... G02C 7/022; G02C 7/02; G02C 7/021; G02C 7/04; G02C 7/044; G02C 7/16;
(Continued)

(56) References Cited

U.S. PATENT DOCUMENTS

| 149,270 A | 3/1847 | Watson |
| 338,003 A | 3/1886 | Ward |

(Continued)

FOREIGN PATENT DOCUMENTS

| AU | 2005289302 | 4/2006 |
| CN | 1909860 | 2/2007 |

(Continued)

OTHER PUBLICATIONS

Ahem "Biochemical, reagents kits offer scientists good return on investment," The Scientist, Jul. 1995, 9(15):20.
(Continued)

*Primary Examiner* — Jordan M Schwartz
(74) *Attorney, Agent, or Firm* — McDonnell Boehnen Hulbert & Berghoff

(57) ABSTRACT

Eyeglasses are disclosed that include eyeglass frames and a pair of ophthalmic lenses mounted in the frames. The lenses include a dot pattern distributed across each lens, the dot pattern including an array of dots spaced apart by a distance of 1 mm or less, each dot having a maximum dimension of 0.3 mm or less, the dot pattern including a clear aperture free of dots having a maximum dimension of more than 1 mm, the clear aperture being aligned with a viewing axis of a wearer of the pair of eyeglasses.

15 Claims, 15 Drawing Sheets

Related U.S. Application Data continuation of application No. PCT/US2017/044635, filed on Jul. 31, 2017.

(60) Provisional application No. 62/502,995, filed on May 8, 2017, provisional application No. 62/369,351, filed on Aug. 1, 2016.

(51) Int. Cl.
  *G02C 7/16* (2006.01)
  *B29D 11/00* (2006.01)
  *G02C 7/10* (2006.01)
  *A61B 3/10* (2006.01)

(52) U.S. Cl.
  CPC .............. *G02C 7/021* (2013.01); *G02C 7/04* (2013.01); *G02C 7/10* (2013.01); *G02C 7/16* (2013.01); *A61B 3/1005* (2013.01); *G02C 2202/24* (2013.01)

(58) Field of Classification Search
  CPC ............... G02C 7/165; G02C 2202/24; B29D 11/00317; B29D 11/00326; B29D 11/00336
  See application file for complete search history.

(56) References Cited

U.S. PATENT DOCUMENTS

| | | | |
|---|---|---|---|
| 506,983 | A | 10/1893 | Diemmer et al. |
| 712,466 | A | 10/1902 | Taylor |
| 1,959,915 | A | 5/1934 | Guthrie |
| 3,507,566 | A | 4/1970 | Knapp |
| 4,194,814 | A | 3/1980 | Fischer et al. |
| 4,338,003 | A | 7/1982 | Adrian |
| 4,704,016 | A | 11/1987 | de Carle |
| 4,710,327 | A | 12/1987 | Neefe |
| 4,889,421 | A * | 12/1989 | Cohen .................... G02C 7/046 351/159.3 |
| 4,909,818 | A | 3/1990 | Jones |
| 5,034,100 | A | 7/1991 | Sides |
| 5,044,742 | A | 9/1991 | Cohen |
| 5,116,112 | A * | 5/1992 | Rawlings ................ G02B 1/043 351/159.29 |
| 5,260,727 | A | 11/1993 | Oksman et al. |
| 5,585,968 | A * | 12/1996 | Guhman .............. G02B 3/0087 385/33 |
| 5,800,992 | A | 9/1998 | Fodor et al. |
| 5,837,461 | A | 11/1998 | Neitz |
| 5,867,247 | A | 2/1999 | Martin et al. |
| 5,905,561 | A | 5/1999 | Lee et al. |
| 5,926,250 | A | 7/1999 | Mukaiyama et al. |
| 6,149,270 | A | 11/2000 | Hayashi |
| 6,343,861 | B1 | 2/2002 | Kris et al. |
| 6,582,908 | B2 | 6/2003 | Fodor et al. |
| 6,706,867 | B1 | 3/2004 | Lorenz |
| 6,712,466 | B2 | 3/2004 | Dreher |
| 6,712,467 | B1 | 3/2004 | Kitani |
| 6,754,299 | B2 | 6/2004 | Patch |
| 6,997,554 | B2 | 2/2006 | Nakada et al. |
| 7,025,460 | B2 | 4/2006 | Smitth et al. |
| 7,506,983 | B2 | 3/2009 | To et al. |
| 7,604,351 | B2 | 10/2009 | Fukuma et al. |
| 7,766,482 | B2 | 8/2010 | Smith et al. |
| 7,862,171 | B2 | 1/2011 | Varnas et al. |
| 7,901,075 | B2 | 3/2011 | Rooney et al. |
| 7,992,997 | B2 | 8/2011 | Varnas |
| 7,997,727 | B2 | 8/2011 | Ho et al. |
| 8,052,278 | B2 | 11/2011 | Bovet et al. |
| 8,057,034 | B2 | 11/2011 | Ho et al. |
| 8,079,702 | B2 | 12/2011 | Ballet et al. |
| 8,115,792 | B2 | 2/2012 | Petsch et al. |
| 8,162,477 | B2 | 4/2012 | Carimalo et al. |
| 8,240,847 | B2 | 8/2012 | Holden et al. |
| RE43,851 | E | 12/2012 | To et al. |
| 8,342,684 | B2 | 1/2013 | Ho et al. |
| 8,500,278 | B2 | 8/2013 | Lo et al. |
| 8,540,365 | B2 | 9/2013 | Varnas |
| 8,684,520 | B2 | 4/2014 | Lindacher et al. |
| 8,690,319 | B2 | 4/2014 | Menezes |
| 8,807,747 | B2 | 8/2014 | Guilloux et al. |
| RE45,147 | E | 9/2014 | To et al. |
| 8,833,936 | B2 | 9/2014 | Varnas |
| 8,926,092 | B2 | 1/2015 | Weeber |
| 8,931,897 | B2 | 1/2015 | Holden et al. |
| 8,950,860 | B2 | 2/2015 | Tse et al. |
| 8,951,729 | B2 | 2/2015 | Neitz et al. |
| 8,992,010 | B2 | 3/2015 | Ho et al. |
| 8,998,408 | B2 | 4/2015 | Wei et al. |
| 9,360,683 | B2 | 6/2016 | Buehren |
| 9,417,463 | B2 | 8/2016 | Brennan et al. |
| 9,423,633 | B2 | 8/2016 | Ho et al. |
| 9,547,182 | B2 | 1/2017 | Collins et al. |
| 9,594,259 | B2 | 3/2017 | Brennan et al. |
| 9,625,739 | B2 | 4/2017 | Brennan et al. |
| 9,709,819 | B2 | 7/2017 | Lippens et al. |
| 9,720,253 | B2 | 8/2017 | Neitz et al. |
| 9,733,494 | B2 | 8/2017 | Brennan et al. |
| 9,746,693 | B2 | 8/2017 | Peloux et al. |
| 9,829,722 | B2 | 11/2017 | Tse et al. |
| 10,012,849 | B2 | 7/2018 | Collins et al. |
| RE47,006 | E | 8/2018 | To et al. |
| 10,042,091 | B2 | 8/2018 | Kildishev et al. |
| 10,061,143 | B2 | 8/2018 | Brennan et al. |
| 10,156,737 | B2 | 12/2018 | Martinez et al. |
| 10,203,522 | B2 | 2/2019 | Bakaraju et al. |
| 10,231,897 | B2 | 3/2019 | Tse et al. |
| 10,247,964 | B2 | 4/2019 | Sankaridurg et al. |
| 10,302,962 | B2 | 5/2019 | Neitz et al. |
| 10,429,670 | B2 | 10/2019 | Newman |
| 10,571,717 | B2 | 2/2020 | Neitz et al. |
| 10,787,707 | B2 | 9/2020 | Neitz et al. |
| 10,795,181 | B2 | 10/2020 | Neitz et al. |
| 10,884,264 | B2 | 1/2021 | Hones et al. |
| 11,048,102 | B2 | 6/2021 | Neitz |
| 2002/0140900 | A1 | 10/2002 | Streibig |
| 2003/0082576 | A1 | 5/2003 | Jones et al. |
| 2004/0110179 | A1 | 6/2004 | Shuber |
| 2004/0150787 | A1 | 8/2004 | Niculas et al. |
| 2005/0208555 | A1 | 9/2005 | Raimond |
| 2006/0082729 | A1 | 4/2006 | To et al. |
| 2006/0118263 | A1 * | 6/2006 | Silvestrini ................ A61F 2/15 623/6.31 |
| 2006/0235428 | A1 | 10/2006 | Silvestrini |
| 2006/0285071 | A1 | 12/2006 | Erickson et al. |
| 2007/0026167 | A1 | 2/2007 | Bourdelais et al. |
| 2007/0115431 | A1 | 5/2007 | Smith et al. |
| 2007/0247588 | A1 | 10/2007 | Cano |
| 2007/0296916 | A1 | 12/2007 | Holden et al. |
| 2008/0030675 | A1 | 2/2008 | Dillon |
| 2008/0084534 | A1 | 4/2008 | Lindacher et al. |
| 2008/0151183 | A1 | 6/2008 | Altmann |
| 2008/0221674 | A1 | 9/2008 | Blum et al. |
| 2008/0309882 | A1 | 12/2008 | Thom et al. |
| 2009/0059168 | A1 | 3/2009 | Miller et al. |
| 2009/0115962 | A1 | 5/2009 | Bovet et al. |
| 2010/0021889 | A1 | 1/2010 | Juo |
| 2010/0091240 | A1 | 4/2010 | Drobe |
| 2010/0149488 | A1 | 6/2010 | Lo et al. |
| 2011/0051079 | A1 | 3/2011 | Martinez et al. |
| 2011/0194195 | A1 | 8/2011 | Zalevsky et al. |
| 2011/0313058 | A1 | 12/2011 | Neitz et al. |
| 2012/0014977 | A1 | 1/2012 | Furihata |
| 2012/0062836 | A1 | 3/2012 | Tse et al. |
| 2012/0182520 | A1 | 7/2012 | Neitz et al. |
| 2013/0053425 | A1 | 2/2013 | To et al. |
| 2013/0103147 | A1 | 4/2013 | Christie et al. |
| 2013/0107206 | A1 | 5/2013 | Slater |
| 2014/0080900 | A1 | 3/2014 | Neitz et al. |
| 2014/0111763 | A1 | 4/2014 | Griffin |
| 2015/0036102 | A1 | 2/2015 | Ghosh et al. |
| 2015/0109574 | A1 | 4/2015 | Tse et al. |
| 2015/0111782 | A1 | 4/2015 | Neitz et al. |
| 2015/0160477 | A1 | 6/2015 | Dai et al. |

(56) References Cited

U.S. PATENT DOCUMENTS

| | | |
|---|---|---|
| 2015/0316788 A1 | 11/2015 | Holden et al. |
| 2015/0331255 A1 | 11/2015 | Sankaridurg et al. |
| 2016/0026000 A1 | 1/2016 | Kester |
| 2016/0143801 A1 | 5/2016 | Lam et al. |
| 2016/0377884 A1 | 12/2016 | Lau et al. |
| 2017/0115509 A1 | 4/2017 | Brennan et al. |
| 2017/0131567 A1 | 5/2017 | To et al. |
| 2017/0168320 A1 | 6/2017 | Tsubota |
| 2017/0184875 A1 | 6/2017 | Newman |
| 2017/0189168 A1 | 7/2017 | Zickler et al. |
| 2017/0192252 A1 | 7/2017 | Brennan et al. |
| 2017/0276963 A1 | 9/2017 | Brennan et al. |
| 2017/0292160 A1 | 10/2017 | Neitz et al. |
| 2017/0336653 A1 | 11/2017 | Bakaraju |
| 2018/0112268 A1 | 4/2018 | Neitz et al. |
| 2018/0275425 A1 | 9/2018 | Collins et al. |
| 2018/0275427 A1 | 9/2018 | Lau et al. |
| 2019/0033619 A1 | 1/2019 | Neitz et al. |
| 2019/0235279 A1 | 8/2019 | Hones et al. |
| 2019/0302477 A1 | 10/2019 | Neitz et al. |
| 2020/0073147 A1 | 3/2020 | Bakaraju et al. |
| 2020/0089023 A1 | 3/2020 | Zhou et al. |
| 2020/0393699 A1 | 12/2020 | Neitz |
| 2021/0165244 A1 | 6/2021 | Hones et al. |
| 2021/0341753 A1 | 11/2021 | Neitz |
| 2022/0035179 A1 | 2/2022 | Rappon et al. |

FOREIGN PATENT DOCUMENTS

| | | |
|---|---|---|
| CN | 2924572 | 7/2007 |
| CN | 101198434 | 6/2008 |
| CN | 101273882 | 10/2008 |
| CN | 101595420 | 12/2009 |
| CN | 101730500 | 6/2010 |
| CN | 102238927 | 11/2011 |
| CN | 103097940 | 5/2013 |
| CN | 103959138 | 7/2014 |
| CN | 104094164 | 10/2014 |
| CN | 104094165 | 10/2014 |
| CN | 104 678 572 A | 6/2015 |
| CN | 105378545 | 3/2016 |
| EP | 0457612 | 11/1991 |
| EP | 1799166 | 6/2007 |
| EP | 2131721 | 12/2009 |
| EP | 2616876 | 7/2013 |
| EP | 2 962 155 | 1/2016 |
| EP | 2548533 | 2/2018 |
| EP | 3614981 | 3/2020 |
| EP | 3 667 401 | 6/2020 |
| EP | 3 746001 | 12/2020 |
| EP | 3931626 | 1/2022 |
| HK | 1210838 | 5/2016 |
| JP | S5829627 | 2/1983 |
| JP | 2004514921 | 5/2004 |
| JP | 2008040497 | 2/2008 |
| JP | 2008514318 | 5/2008 |
| JP | 4891249 | 3/2012 |
| JP | 2013537317 | 9/2013 |
| JP | 2017510851 | 4/2017 |
| JP | 2019529968 | 10/2019 |
| JP | 2012513252 | 7/2021 |
| KR | 100686551 | 2/2007 |
| KR | 100840845 | 6/2008 |
| TW | 279510 | 6/1996 |
| TW | 201211618 | 3/2012 |
| TW | 201307942 | 2/2013 |
| TW | 1530727 | 4/2016 |
| TW | 1559044 | 11/2016 |
| TW | 1561885 | 12/2016 |
| WO | WO 86/06846 | 11/1986 |
| WO | 97/31286 | 8/1997 |
| WO | 99/66366 | 12/1999 |
| WO | 00/52516 | 9/2000 |
| WO | WO 2002/031585 | 4/2002 |
| WO | WO 2006/034652 | 4/2006 |
| WO | 2006/113149 | 10/2006 |
| WO | 2007/082268 | 7/2007 |
| WO | WO 2007/132834 | 11/2007 |
| WO | WO 2008/026674 | 3/2008 |
| WO | 2008/045847 | 4/2008 |
| WO | 2008/059178 | 5/2008 |
| WO | 2008/083418 | 7/2008 |
| WO | 2010/019397 | 2/2010 |
| WO | WO 2010/075319 | 7/2010 |
| WO | 2010/088644 | 8/2010 |
| WO | WO2011/031948 | 3/2011 |
| WO | 2012/034265 | 3/2012 |
| WO | WO2012/097213 | 7/2012 |
| WO | 2013/015743 | 1/2013 |
| WO | WO 2013/082545 | 6/2013 |
| WO | 2013/134825 | 9/2013 |
| WO | WO 2014/194444 | 12/2014 |
| WO | 2015/055322 | 4/2015 |
| WO | 2015/147758 A1 | 10/2015 |
| WO | 2015/186723 | 12/2015 |
| WO | WO2016/138512 | 9/2016 |
| WO | 2017/178430 | 10/2017 |
| WO | 2018/026697 | 2/2018 |
| WO | 2018/076057 | 5/2018 |
| WO | 2018/208724 | 11/2018 |
| WO | WO 2019/166653 | 9/2019 |
| WO | WO 2020/13 8127 | 7/2020 |

OTHER PUBLICATIONS

Applied Biosystems—Product Bulletin—Automated DNA Sequencing [online] "ABI PRISM® BigDyeTM Primer Sequencing Kit," 2000, available via url: <tools.thermofisher.com/content/sfs/brochures/cms_040730.pdf>, 4 pages.

Carkeet et al., "Repeatability of IOLMaster Biometry in Children, Optometry and Vision Science", Nov. 2004, 81(11) : 829-834.

Carroll et al., "Estimates of L:M cone ratio from ERG flicker photometry and genetics", Journal of Vision, 2002, 2(8):531-542.

Carroll et al., "Cone photoreceptor mosaic disruption associated with Cys203Arg mutation in the M-cone opsin," Proceedings of the National Academy of Sciences of the United States of America, 2009, 106(49):20948-20953.

Carroll, et al., "Functional photoreceptor loss revealed with adaptive optics: An alternate cause of color blindness," Proceedings of the National Academy of Sciences of the United States of America, 2004, 101(22):8461-8466.

Carroll, J., McMahon, C., Neitz, M., & Neitz, J. (2000). Flicker-photometric electroretinogram estimates of L: M cone photoreceptor ratio in men with photopigment spectra derived from genetics. Journal of The Optical Society ofAmerica A, 17,499-509.

Crognale et al., "Characterization of a novel form of X-linked incomplete achromatopsia", Visual Neuroscience, 2004, 21(3):197-203.

Davidoff, "Cone opsin gene variants in color blindness and other vision disorders," 2015, Retrieved from the Internet: <https://digital.lib.washington.edu/researchworks/bitstream/handle/1773/33578/Davidoff_washington_0250E_15133.pdf?sequence=1&isAllowed=y>, 132 pages.

Drummond-Borg, et al., "Molecular patterns of X chromosome-linked color vision genes among 134 men of European ancestry," Proceedings of the National Academy of Sciences of the United States of America, Feb. 1989, 86:983-987.

EP Extended European Search Report in European Appln. No. 19747437.2, dated Mar. 16, 2021, 10 pages.

Gardner et al., "Three Different Cone Opsin Gene Array Mutational Mechanisms with Genotype-Phenotype Correlation and Functional Investigation of Cone Opsin Variants" Human Mutation (2014) vol. 35(11), pp. 1354-1362.

GeneCards [online], "GeneCard for the OPN1MW gene", retrieved on Apr. 6, 2020, retrieved from <genecards.org/cgi-bin/carddisp_pl?gene=OPN1 MW>, 27 pages.

Greenwald et al., "Role of a Dual Splicing and Amino Acid Code in Myopia, Cone Dysfunction and Cone Dystrophy Associated with

(56) References Cited

OTHER PUBLICATIONS

L/M Opsin Interchange Mutations," Translation Vision Science & Technology, vol. 6, No. 3, dated May 10, 2017, 19 pages.
Gunther et al., "Individual differences in chromatic (red/green) contrast sensitivity are constrained by the relative number of L-versus M-cones in the eye", Vision Research, May 2002, 42(11):1367-1378.
Gwiazda et al., "A Randomized Clinical Trial of Progressive Addition Lenses versus Single Vision Lenses on the Progression of Myopia in Children", Investigative Ophthalmology & Visual Science, Apr. 2003, 44:1492-1500.
Hahner et al., "Strategies for SNP genotyping by mass spectrometry", International Congress Series, Jan. 2003, 1239: 11-16.
Halushka et al., "Patterns of single-nucleotide polymorphisms in candidate genes for blood-pressure homeostasis", Nat Genet, 1999, 239-247.
Hattersleydm et al., "What makes a good genetic association study?" The Lancet, Oct. 2005, 366(9493):1315-1323.
Hirschhom et al. "A comprehensive review of genetic association studies", Genet Med, 2002, 45-61.
Hofer, et al., "Organization of the Human Trichromatic Cone Mosaic" Journal of Neuroscience, Oct. 19, 2005, 25(42):9669-9679.
Kuchenbecker et al., "Topography of the long- to middle-wavelength sensitive cone ratio in the human retina assessed with a wide-field color multifocal electroretinogram", Vis Neurosci, May-Jun. 2008, 25(3):301-6.
Lucentini, "Gene association studies typically wrong: reproducible gene-disease associations are few and far between", The Scientist, 2004, 18(24): p. 20.
McClements et al., (2010) "The PROM1 mutation p.R373C causes an autosomal dominant bull's eye maculopathy associated with rod, rod-cone, and macular dystrophy," IOVS, 51(9): 4771-4780.
McClements, Michelle et al. Variations in Opsin Coding Sequences Cause X-Linked Cone Dysfunction Syndrome, with Myopia and Dichromacy Investigative Ophthalmology & Visual Science (2013) vol. 54(2), pp. 1361-1369.
McMahon et al., "The L:M cone ratio in males of African descent with normal color vision", Journal of Vision, 2008, 8(2):1-9.
Michaelides et al., "X-Linked Cone Dysfunction Syndrome with Myopia and Protanopia" Ophthalmology, Aug. 2005, 112(8): 1448-1454.
Michaelides, et al. (2010) "The PROM1 mutation p.R373C causes an autosomal dominant bull's eye maculopathy associated with rod, rod-cone, and macular dystrophy," IOVS, 51(9): 4771-4780.
Mizrahi-Meissonnier et al., "Variable Retinal Phenotypes Caused by Mutations in the X-Linked Photopigment Gene Array", Investigative Ophthalmology & Visual Science, Aug. 2010, (51):3884-3892.
Mummidi et al., "Evolution of Human and Non-human Primate CC Chemokine Receptor 5 Gene and mRNA,Potential Roles for Haplotype and mRNA Diversity, Differential Haplotype-Specific Transcriptional Activity, and Altered Transcription Factor Binding To Polymorphic Nucleotides in the Pathogenesis of HIV-1 and Simian Immunodeficiency VIRUS*210", Journal of Biological Chemistiy, 2000, 275(25):18946-18961.
Nathans et al., "Molecular Genetics of Human Blue Cone Monochromacy", Aug. 1989, 45(4920): pp. 831-838.
Nathans et al., "Molecular Genetics of Inherited Variation in Human Color Vision", Apr. 1986, 232(4747): pp. 203-210.
NCBI Database GenBank Accession No. NM 020061. Nov. 1, 2009. National Center for Biotechnology Information, National Library of Medicine, Bethesda, MD, USA), 7 pages.
Neitz et al., "Cone mosaic disruption caused by L/M opsin mutations in bomholm eye disease," ARVO Annual Meeting Abstract, Apr. 2011, 2 pages.
Neitz et al. "Variety of genotypes in males diagnosed as dichromatic on a conventional clinical anomaloscope", Visual Neuroscience, 2004, 21(3):205-216.
Neitz et al., "Polymorphism in the number of genes encoding long-wavelength-sensitive cone pigments among males with normal color vision", Vision Research, Sep. 1995, 35(17): 2395-2407.
Neitz, "A new mass screening test for color-vision deficiencies in children" Color Research & Application, 2001, 26(1): S239-S249.
Oda, et al. (2003) "Analysis of L-cone/M-cone visual pigment gene arrays in females by long-range PCR" Visior Research, vol. 43, pp. 489-495.
Radhakrishna, et al., "The 'X-linked' severe form of myopia locus at Xq28 (MYP1): Narrowing of the critical region and exclusion of twelve known genes localized in the interval.", ARVO Annual Meeting Abstract, May 2005, 1 page.
Scholl, et al., (2001) "Macular dystrophy with protan genotype and phenotype studied with cone type specific ERGs" Current Eye Research, vol. 22(3) pp. 221-228.
Scholl, et al., (2006) "Progressive cone dystrophy with deutan genotype and phenotype", Graefe's Arch Clin Exp Ophthalmol, vol. 244, pp. 183-191.
Schwartz et al., "X-linked myopia: Bomholm Eye Disease", Clinical Genetics, 1990, 38(4):281-286.
Twelker et al., "Children's Ocular Components and Age, Gender, and Ethnicity", Optometry and Vision Science, Aug. 2009, 86(8):918-935.
Ueyama, Hisao et al. "Unique haplotype in exon 3 of cone opsin mRNA affects splicing of its precursor, leading to congenital color vision defect" Biochemical and Biophysical Research Communications (2012) vol. 424, pp. 152-157.
Verrelli et al., "Signatures of Selection and Gene Conversion Associated with Human Color Vision Variation", The American Journal of Human Genetics, 2004,75(3): 363-375.
Winderickx et al., "Defective colour vision associated with a missense mutation in the human green visual pigment gene", Nat Genet 1992, 251-256.
Winderickx, et al. (1993) "Haplotype diversity in the human red and green opsin genes: evidence for frequent sequence exchange in exon 3," Human Molecular Genetics, 2(9):1413-1421.
Young, et al., (2001) "Further refinement of the MYP2 locus for autosomal dominant high myopia by linkage disequilibrium analysis", Ophthalmic Genetics, vol. 22, pp. 69-75.
Young et al., "X-Linked High Myopia Associated With Cone Dysfunction", Arch Ophthalmol. 2004, 122(6):897-908.
The International Search Report (ISR) with Written Opinion for PCT/US2017/044635 dated Nov. 14, 2017, pp. 1-33.
Okada et al., "Target Spatial Frequency Determines the Response to Conflicting Defocus—and Convergence—Driven Accommodative Stimuli," 2006 Elsevier, vol. 46, pp. 475-484.
Montana.edu [online] SHAW, "Optical System Design—S15," [Retrieved on Jan. 7, 2019], Retrieved from: http://www.montana.edu/jshaw/documents/18%20EELE582_S15_OTFMTF.pdf, 18 pages.
Slrlounge.com [online] JIRSA, "Diffraction, Aperture, and Starburst Effects," dated Feb. 9, 2011, [Retrieved on Jan. 7, 2019] Retrieved from: https://www.slrlounge.com/diffraction-aperture-and-starburst-effects/, 11 pages.
PCT International Preliminary Report on Patentability in International Application No. PCT/US2017/044635, dated Feb. 14, 2019, 13 Pages.
Anstice et al., "Effect of dual-focus soft contact lens wear on axial myopia progression in children," Ophthalmology, 2011, 1152-1161.
Brennan et al., "Commonly held beliefs about myopia that lack a robust evidence base," Eye & Contact Lens, Jul. 2019, 45(4):215-225.
Chamberlain et al., "A 3-year Randomized Clinical Trial of MiSight Lenses for Myopia Control", Optom Vis Sci, 2019, 96(8): 556-567.
Cheng et al., "Effect of Bifocal and Prismatic Bifocal Spectacles on Myopia Progression in Children: Three-Year Results of a Randomized Clinical Trial", JAMA Ophthalmology, Mar. 2014, 132(3):258-264.
Cheng et al., "Soft contact lenses with positive spherical aberration for myopia control," Optometry and Vision Science, Apr. 2016, 93(4):353-366.
Jones et al., "The Prevalence and Impact of High Myopia," Eye & Contact Lens, May 2012, 38(3):188-96.

(56) References Cited

OTHER PUBLICATIONS

Ruiz-Pomeda et al., "MiSight Assessment Study Spain (MASS). A 2-year randomized clinical trial," Graefe's Archive for Clinical and Experimental Ophthalmology, Feb. 3, 2018, 256:1011-1021.

Sankaridurg et al., "Decrease in rate of myopia progression with a contact lens designed toreduce relative peripheral huperopia: One-year results," IOVS, Dec. 2011, 52(13):9362-9367.

Tedja et al., "Genome-wide association meta-analysis highlights light-induced signaling as a driver for refractive error", Nature Genetics, Jun. 2018, 50(6):834-848.

Vitale et al., "Increased prevalence of myopia in the United States between 1971-1972 and 1999-2004," Arch Ophthalmol., Dec. 2009, 127(12):1632-1639.

Zhang, "Genetics of Refraction and Myopia", Progress in Molecular Biology and Translational Science, 2015, 134: 269-279.

\* cited by examiner

FIG. 2

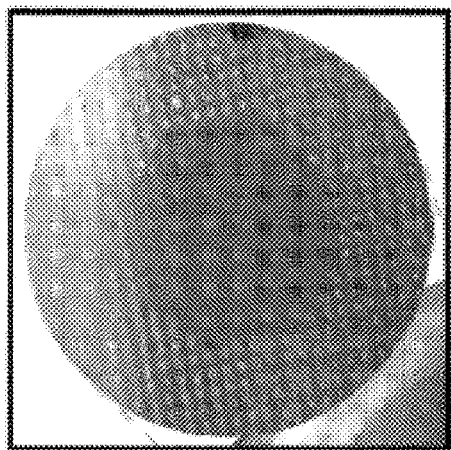
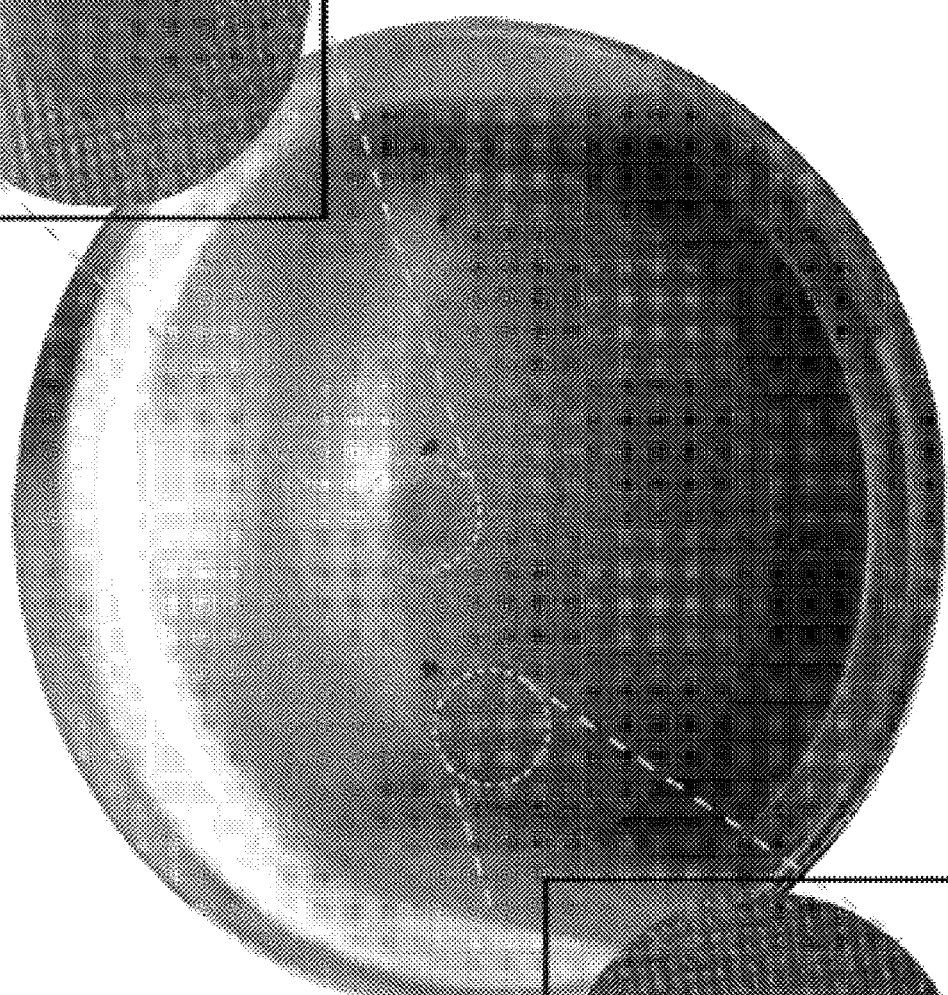
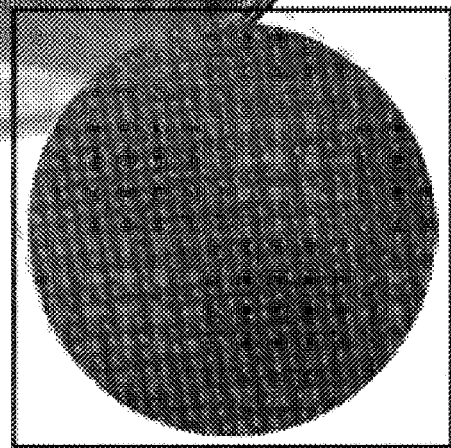

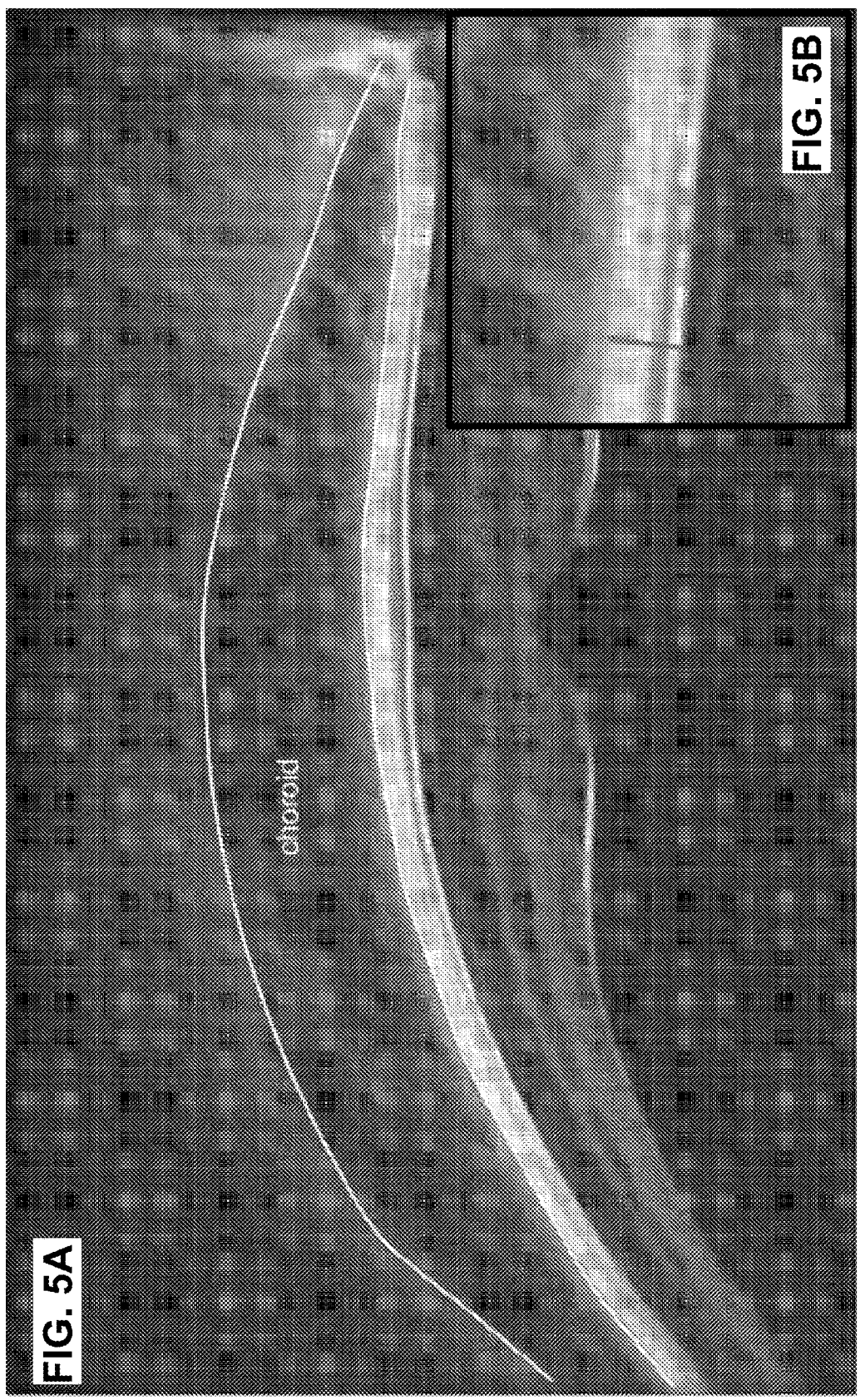

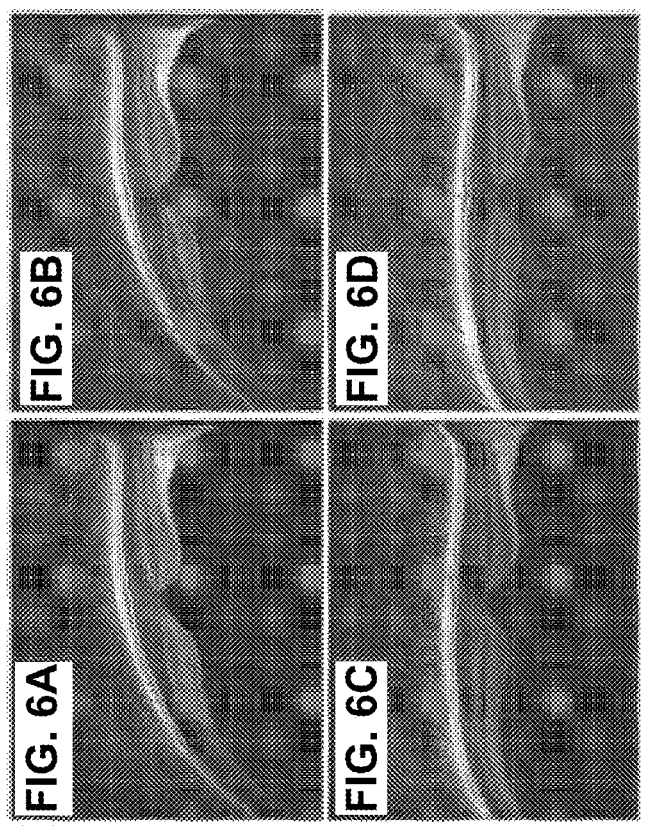
FIG. 6A  FIG. 6B
FIG. 6C  FIG. 6D
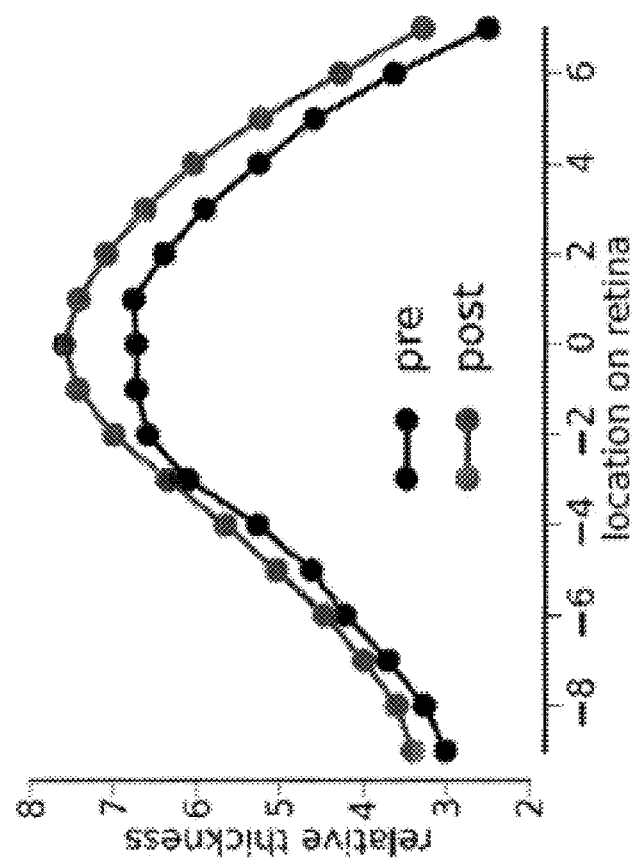
FIG. 7

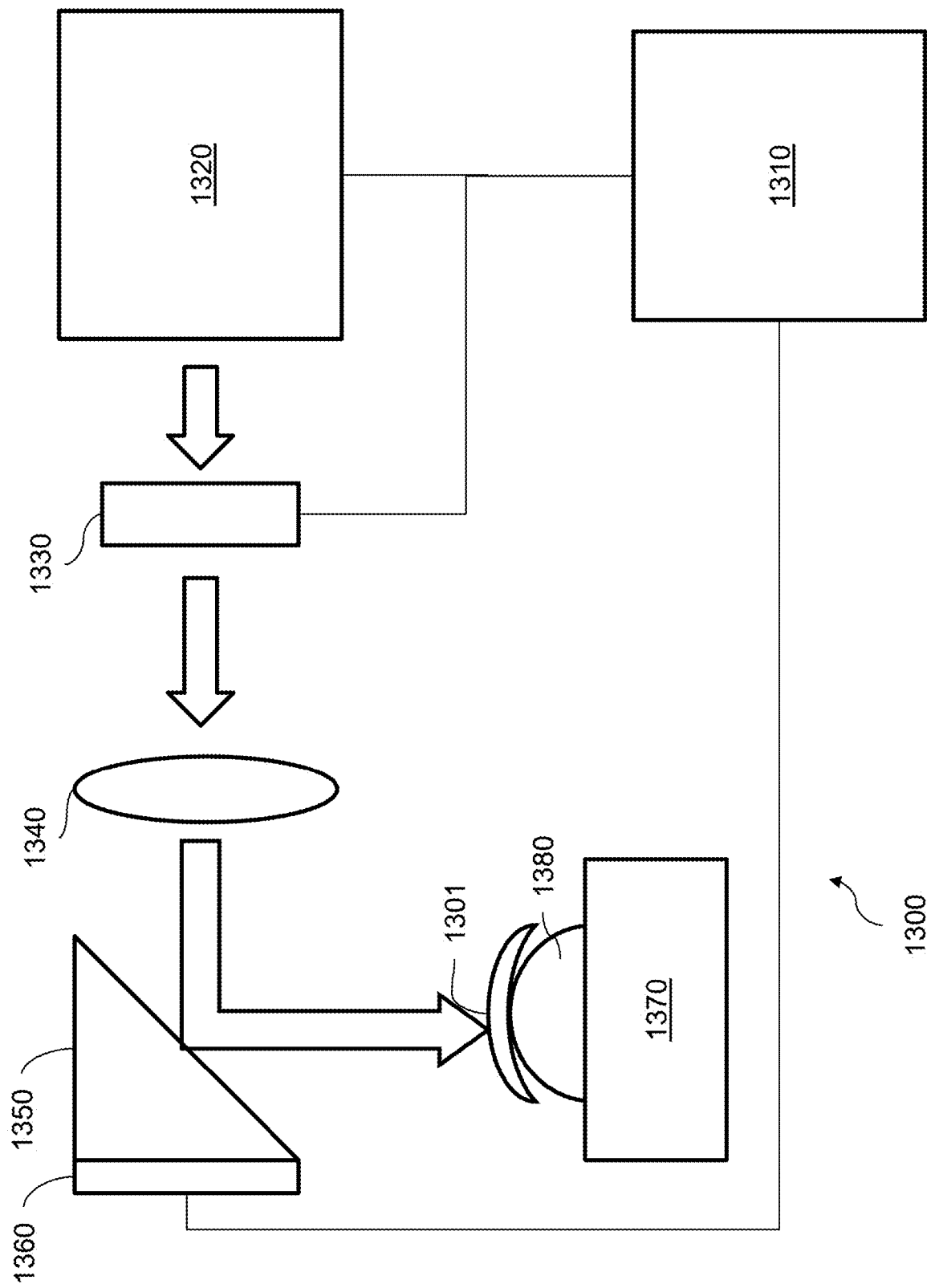

OPHTHALMIC LENSES FOR TREATING MYOPIA

CROSS REFERENCE

This application is a continuation of U.S. patent application Ser. No. 16/143,707 filed Sep. 27, 2018, which is a continuation of PCT application Serial Number PCT/US2017/044635 filed Jul. 31, 2017, which claims priority to U.S. Provisional Application Ser. No. 62/369,351 filed Aug. 1, 2016 and 62/502,995 filed May 8, 2017.

FIELD OF THE INVENTION

The invention features ophthalmic lenses for treating myopia, methods for forming such lenses, methods for using such lenses, and methods for monitoring the efficacy of such lenses.

BACKGROUND

The eye is an optical sensor in which light from external sources is focused, by a lens, onto the surface of the retina, an array of wavelength-dependent photosensors. Each of the various shapes that the eye lens can adopt is associated with a focal length at which external light rays are optimally or near-optimally focused to produce inverted images on the surface of the retina that correspond to external images observed by the eye. The eye lens, in each of the various shapes that the eye lens can adopt, optimally or near-optimally, focuses light emitted by, or reflected from external objects that lie within a certain range of distances from the eye, and less optimally focuses, or fails to focus objects that lie outside that range of distances.

In normal-sighted individuals, the axial length of the eye, or distance from the lens to the surface of the retina, corresponds to a focal length for near-optimal focusing of distant objects. The eyes of normal-sighted individuals focus distant objects without nervous input to muscles which apply forces to alter the shape of the eye lens, a process referred to as "accommodation." Closer, nearby objects are focused, by normal individuals, as a result of accommodation.

Many people, however, suffer from eye-length-related disorders, such as myopia ("nearsightedness"). In myopic individuals, the axial length of the eye is longer than the axial length required to focus distant objects without accommodation. As a result, myopic individuals can view near objects clearly, but objects further away are blurry. While myopic individuals are generally capable of accommodation, the average distance at which they can focus objects is shorter than that for normal-sighted individuals.

Typically, infants are born hyperopic, with eye lengths shorter than needed for optimal or near-optimal focusing of distant objects without accommodation. During normal development of the eye, referred to as "emmetropization," the axial length of the eye, relative to other dimensions of the eye, increases up to a length that provides near-optimal focusing of distant objects without accommodation. Ideally, biological processes maintain the near-optimal relative eye length to eye size as the eye grows to final, adult size. However, in myopic individuals, the relative axial length of the eye to overall eye size continues to increase during development past a length that provides near-optimal focusing of distant objects, leading to increasingly pronounced myopia.

It is believed that myopia is affected by behavioral factors as well as genetic factors. Accordingly, myopia may be mitigated by therapeutic devices which address behavioral factors. For example, therapeutic devices for treating eye-length related disorders, including myopia, are described in U.S. Pub. No. 2011/0313058A1.

SUMMARY

Eyeglasses and contact lenses are disclosed that reduce signals in the retina responsible for growth of eye length. Exemplary embodiments are made using polycarbonate or Trivex lens blanks which have been treated by applying a pattern of clear liquid plastic protuberances that that are hardened and bonded to the lens by ultraviolet light. Each clear plastic protuberance has a refractive index similar to the underlying polycarbonate to which it is bonded so in the location of the protuberance it and the underlying lens act as a single optical element. The array of such optical elements behave as a highly aberrated lens array dispersing light transmitted by the array fairly uniformly in all directions. The result is a reduction in contrast in a retinal image. The eyeglass lenses have apertures free from protuberances located on the lens axes allowing a user to experience maximal visual acuity when viewing on-axis objects, while objects in the periphery of the user's visual field are viewed with reduced contrast and acuity.

In one example, an image on the retina consists of the normally focused image with an average intensity of 74% of what would be produced by the lens without the protuberance array. Superimposed on the focused image is a background of uniform retinal illumination equal to 25% of the average luminance of the normally focused image.

For these eyeglasses, the focused image is reduced in contrast compared to that normally used to correct (but not treat) refractive errors. The exact amount of contrast reduction depends on the relative amount of dark and light areas in the image being transmitted. For the example above, where 24% of the light is dispersed uniformly, the maximum contrast reduction would be 48% where contrast is defined as the Luminance difference/Average luminance. Experiments demonstrate that this amount of reduction in contrast has significant effects on the physiology of the eye related to mechanisms responsible for controlling the growth of eye length.

Various aspects of the invention are summarized as follows:

In general, in a first aspect, the invention features a pair of eyeglasses, including: eyeglass frames; and a pair of ophthalmic lenses mounted in the frames. The lenses include a dot pattern distributed across each lens, the dot pattern including an array of dots spaced apart by a distance of 1 mm or less, each dot having a maximum dimension of 0.3 mm or less.

Implementations of the eyeglasses may include one or more of the following features and/or features of other aspects. For example, each dot can have a maximum dimension of 0.2 mm or less (e.g., 0.1 mm or less, 0.05 mm or less, 0.02 mm or less, 0.01 mm or less). In some embodiments, each dot is substantially the same size. The dots may be spaced apart by 0.8 mm or less (e.g., 0.6 mm or less, 0.5 mm or less, 0.4 mm or less, 0.35 mm or less). The dots may be arranged on a square grid, a hexagonal gird, another grid, or in a semi-random or random pattern. The dots may be spaced at regular intervals, e.g., such as 0.55 mm, 0.365 mm, or 0.24 mm. Alternatively, dot spacing may vary depending on the distance of the dot from the center of the lens. For example, dot spacing may increase monotonically or decrease monotonically as the distance from the center of the lens increases.

The dot pattern can include a clear aperture free of dots having a maximum dimension of more than 1 mm, the clear aperture being aligned with a viewing axis of a wearer of the pair of eyeglasses. The clear aperture can have a maximum dimension (e.g., a diameter) of 2 mm or more (e.g., 3 mm or more, 4 mm or more, 5 mm or more, 6 mm or more, 7 mm or more, 8 mm or more) and up to 1.5 cm (e.g., 1.5 cm or less, 1.4 cm or less, 1.3 cm or less, 1.2 cm or less, 1.1 cm or less, 1.0 cm or less). The clear aperture can be substantially circular or a similar shape, such as octagonal, square, or other polygon shape.

In some embodiments, the dots are protrusions on a surface of the corresponding lens. The protrusions can be formed from a transparent material. In some cases, the transparent material is clear and/or colorless. Alternatively, or additionally, at least some of the transparent material can be tinted (e.g., with a dye that absorbs red wavelengths). The transparent material can have substantially the same refractive index as a lens material. The protrusions can be substantially spherical or semi-spherical.

In certain embodiments, the dots are recesses on a surface of the corresponding lens.

The dots can be inclusions between opposing surfaces of each lens.

The lenses can be clear lenses. In some embodiments, the lenses are tinted lenses.

The dot pattern can reduce an image contrast of an object viewed through the dot pattern by at least 30% (e.g., by at least 35%, by at least 40%, by at least 45%, by at least 50%, by at least 55%, by at least 60%) compared to an image contrast of the object viewed through the clear aperture. In some embodiments, the lenses have optical power to correct a wearer's on-axis vision to 20/20 or better (e.g., 20/15) through the clear aperture, and, for at least a portion of the wearer's peripheral vision through the dot pattern, the lenses correct the wearer's vision to 20/25 or better, 20/30 or better, 20/40 or better, and the like.

In another aspect, the invention features a method of making the eyeglasses, including: depositing discrete portions a material on a surface of the lens corresponding to the dot pattern; and curing the deposited material to provide protrusions on the lens surface forming the dot pattern. The material can be deposited using an inkjet printer. The deposited material can be cured using radiation (e.g., ultraviolet radiation).

In general, in another aspect, the invention features a pair of eyeglasses customized for a wearer, including: eyeglass frames; and a pair of ophthalmic lenses mounted in the frames, the lenses having optical power to correct the wearer's on-axis vision to 20/20 or better, the lenses including a dot pattern distributed across each lens, the dot pattern including an array of dots arranged so that, for at least a portion of the wearer's peripheral vision, the lenses correct the wearer's vision to 20/25 or better and reduce an image contrast by at least 30% compared to on-axis image contrast. Embodiments of the ophthalmic lens may include one or more of the features of other aspects.

In general, in a further aspect, the invention features a pair of eyeglasses customized for a wearer, including: eyeglass frames; and a pair of ophthalmic lenses mounted in the frames, the lenses having optical power to correct the wearer's on-axis vision to 20/20 or better. The eyeglasses include an optical diffuser distributed across each lens, the optical diffuser being configured so that, for at least a portion of the wearer's peripheral vision, the lenses correct the wearer's vision to 20/40 or better, 20/30 or better, or 20/25 or better and reduce an image contrast by at least 30% compared to on-axis image contrast.

Embodiments of the ophthalmic lens may include one or more of the following features and/or features of other aspects. For example, the optical diffuser can include a film laminated on a surface of each lens. The lenses may each include a clear aperture free of the optical diffuser having a maximum dimension of more than 1 mm, the clear aperture being aligned with a viewing axis of a wearer of the pair of eyeglasses.

In general, in a further aspect, the invention features an ophthalmic lens, including: two opposing curved surfaces collectively having an optical power to correct a wearer's on-axis vision to 20/20 or better; and a dot pattern distributed across each lens, the dot pattern comprising an array of spaced apart dots arranged so that, for at least a portion of the wearer's peripheral vision, the lenses correct the wearer's vision to 20/25 or better and reduce an image contrast by at least 30% compared to on-axis image contrast, the dot pattern including a clear aperture free of dots aligned with a viewing axis of the wearer.

Embodiments of the ophthalmic lens may include one or more of the following features and/or features of other aspects. For example, the ophthalmic lens can be an eyeglass lens. Alternatively, in some embodiments, the ophthalmic lens is a contact lens.

In general, in another aspect, the invention features a method of monitoring and arresting myopia progression in a person, including: measuring variations in a thickness of the person's choroid over a period of time; and providing the person with ophthalmic lenses which reduce an image contrast in the person's peripheral vision compared to an on-axis image contrast.

Implementations of the method can include one or more of the following features and/or features of other aspect. For example, the ophthalmic lenses may be provided in eyeglasses of the foregoing aspects. Alternatively, the ophthalmic lenses may be provided as contact lenses. In some implementations, measuring the variations includes measuring a thickness of the person's choroid using Optical Coherence Tomography (OCT).

Among other advantages, disclosed embodiments feature eyeglasses that include features that reduce signals in the retina responsible for growth of eye length on the lenses for both eyes, without diminishing the user's on-axis vision in either eye to an extent that is disruptive to the user. For example, providing a dot pattern that modestly blurs the wearer's peripheral vision while allowing normal on-axis viewing through a clear aperture allows for all-day, everyday use by the wearer. Disclosed embodiments can also provide therapeutic benefits to a user in both eyes using only a single pair of eyeglasses, in contrast to approaches which involve alternating use of different pairs of eyeglasses.

Moreover, the dot patterns can be largely unnoticeable to others, particularly where dot patterns are clear and colorless and/or where contact lenses are used. The subtlety of the dot patterns can result in more consistent use by certain wearers, especially children, who may otherwise be self-conscious during everyday (e.g., at school or otherwise among peers) use of more conspicuous devices.

BRIEF DESCRIPTION OF THE DRAWINGS

FIG. 2 illustrates contrast reduction experienced using exemplary ophthalmic lenses for treating myopia.

FIGS. 4A-4C are photographs showing a dot pattern on an exemplary ophthalmic lens.

FIGS. 5A-B are optical coherence tomographic (OCT) images of an eye showing choroid thickness.

FIGS. 6A-D are OCT images showing choroid thickness.

FIG. 7 is a plot showing relative choroid thickness as a function of retinal position for a subject pre- and post-treatment.

FIG. 13 is a schematic diagram of a laser system for forming a dot pattern on a contact lens.

DETAILED DESCRIPTION

Figure 1A:
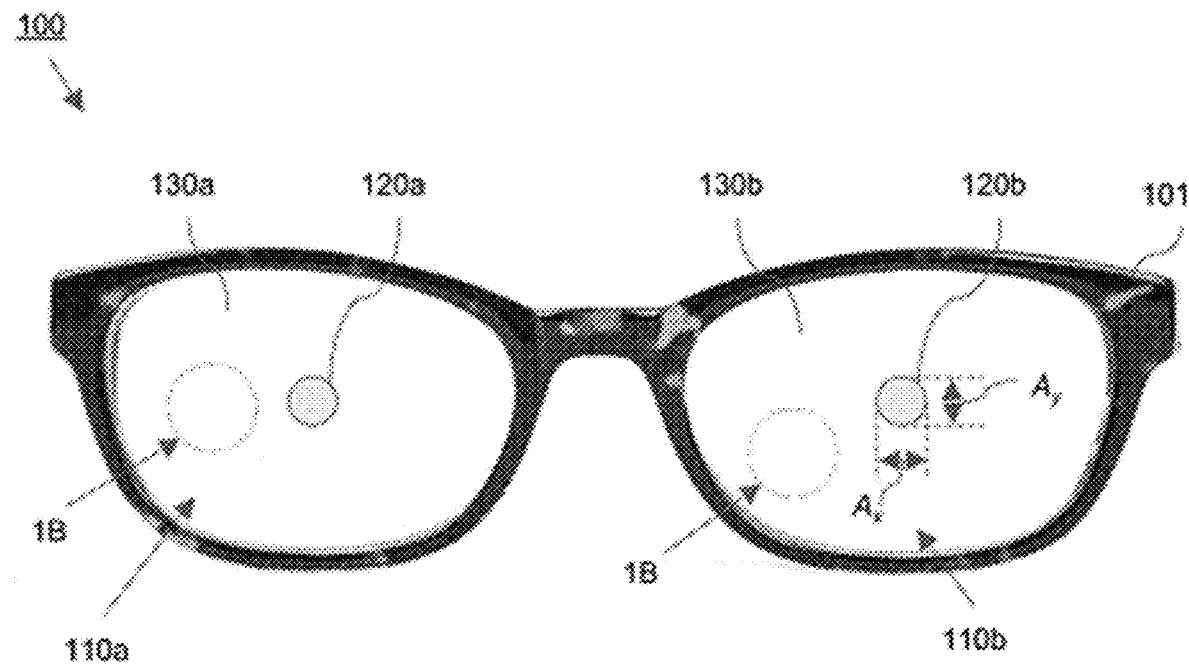
FIG. 1A shows a pair of eyeglasses containing ophthalmic lenses for treating myopia.

Referring to FIG. 1A, myopia-reducing eyeglasses 100 are disclosed which allow treatment of both eyes simultaneously without substantially compromising clear vision. Moreover, the eyeglasses are sufficiently robust and inconspicuous as to allow a wearer to engage in the same day-to-day activities without the eyeglasses failing and without feeling self-conscious about their appearance, which is especially desirable because the eyeglasses are typically used to arrest eye-lengthening in children.

Figure 1B:
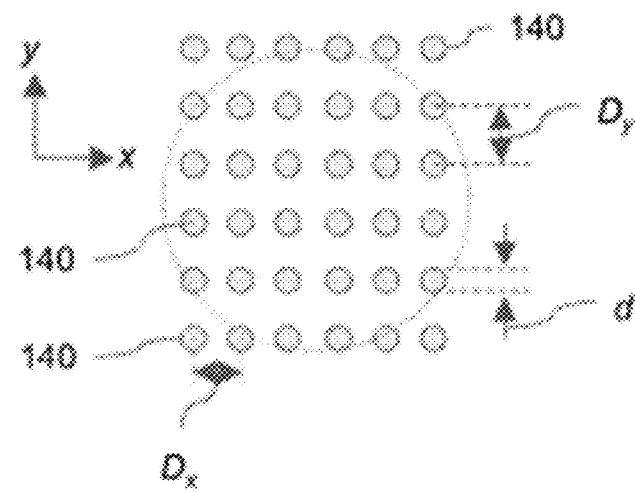
FIG. 1B shows a dot pattern on the ophthalmic lenses shown in FIG. 1A.

Myopia-reducing eyeglasses 100 are composed of a pair of frames 101 and ophthalmic lenses 110a and 110b mounted in the frames. Ophthalmic lenses 110a and 110b each have a clear aperture 120a and 120b, respectively, surrounded by reduced-contrast areas 130a and 130b, respectively. Clear apertures 120a and 120b are positioned to coincide with the wearer's on-axis viewing position, while reduced contrast areas 130a and 130b correspond to the wearer's peripheral vision. Referring also to FIG. 1B, reduced contrast areas 130a and 130b are composed of an array of dots 140, which reduce the contrast of an object in the wearer's peripheral vision by scattering light passing through those areas to the wearer's eye.

The size and shape of the clear aperture may vary. Generally, the clear aperture provides the wearer with a viewing cone for which their visual acuity may be optimally corrected (e.g., to 20/15 or 20/20). In some embodiments, the aperture has a maximum dimension (in the x-y plane) in a range from about 0.2 mm (e.g., about 0.3 mm or more, about 0.4 mm or more, about 0.5 mm or more, about 0.6 mm or more, about 0.7 mm or more, about 0.8 mm or more, about 0.9 mm or more) to about 1.5 cm (e.g., about 1.4 cm or less, about 1.3 cm or less, about 1.2 cm or less, about 1.1 cm or less, about 1 cm or less). Where the aperture is circular, e.g., as depicted in FIG. 1A, this dimension corresponds to the circle's diameter (i.e., $A_x=A_y$), however non-circular (e.g., elliptical, polygonal, $A_x \neq A_y$) apertures are also possible.

The clear aperture can subtend a solid angle of about 30 degrees or less (e.g., about 25 degrees or less, about 20 degrees or less, about 15 degrees or less, about 12 degrees or less, about 10 degrees or less, about 9 degrees or less, about 8 degrees or less, about 7 degrees or less, about 6 degrees or less, about 5 degrees or less, about 4 degrees or less, about 3 degrees or less) in the viewer's visual field. The solid angles subtended in the horizontal and vertical viewing planes may be the same or different.

The dots are formed by arrays of protuberances on a surface of each of lenses 110a and 110b. The protuberances are formed from an optically transparent material having a similar refractive index to the underlying lens, which is 1.60 for polycarbonate. For example, in embodiments where the lenses are formed from polycarbonate, the protuberances can be formed from a polymer having a similar refractive index to the PC, such as from light-activated polyurethane or epoxy based plastics. In addition to PC, the lenses themselves can also be made from allyl diglycol carbonate plastic, a urethane-based monomer or other impact resistant monomers. Alternatively, lenses could be made from one of the more-dense high-refractive index plastics with an index of refraction greater than 1.60.

In some embodiments, the protuberance material is selected to have a refractive index that is within 0.1 (e.g., within 0.09 or less, 0.08 or less, 0.07 or less, 0.06 or less, 0.05 or less, 0.04 or less, 0.03 or less, 0.02 or less, 0.01 or less, 0.005 or less, 0.002 or less, 0.001 or less) of the refractive index of the lens material (e.g., as measured at one or more wavelengths in the visible light range).

The protuberances are sized and shaped so that the dots scatter incident light to reduce contrast of an object viewed through the reduced contrast areas. The protuberances may be substantially spherical, ellipsoidal, or irregularly-shaped. Generally, the protuberances should have a dimension (e.g., diameter, as depicted in FIG. 1B) that is sufficient large to scatter visible light, yet sufficiently small so as not to be resolved by the wearer during normal use. For example, the protuberances can have a dimension (as measured in the x-y plane) in a range from about 0.001 mm or more (e.g., about 0.005 mm or more, about 0.01 mm or more, about 0.015 mm or more, about 0.02 mm or more, about 0.025 mm or more, about 0.03 mm or more, about 0.035 mm or more, about 0.04 mm or more, about 0.045 mm or more, about 0.05 mm or more, about 0.055 mm or more, about 0.06 mm or more, about 0.07 mm or more, about 0.08 mm or more, about 0.09 mm or more, about 0.1 mm) to about 1 mm or less (e.g., about 0.9 mm or less, about 0.8 mm or less, about 0.7 mm or less, about 0.6 mm or less, about 0.5 mm or less, about 0.4 mm or less, about 0.3 mm or less, about 0.2 mm or less, about 0.1 mm).

Note that for smaller protuberances, e.g., having a dimension that is comparable to the wavelength of light (e.g., 0.001 mm to about 0.05 mm), the light scattering may be considered Raleigh or Mie scattering. For larger protuberances, e.g., about 0.1 mm or more, light scattering may be due to a lensing effect of the protuberance, such as due to focusing by a lens with a very small radius of curvature to a point far in front of the user's retina. In such a case, when the light from each protuberance reaches the user's retina, it has substantially diverged from its point of focus and is not resolvable as an image by the user.

In general, the dimension of the protuberances may be the same across each lens or may vary. For example, the dimension may increase or decrease as a function of the location of the protuberance, e.g., as measured from the clear aperture and/or as a function of distance from an edge of the lens. In some embodiments, the protuberance dimensions vary monotonically as the distance from the center of the lens increases (e.g., monotonically increase or monotonically decrease). In some cases, monotonic increase/decrease in dimension includes varying the diameter of the protuberances linearly as a function of the distance from the center of the lens.

The protuberances shown in FIG. 1B are arranged on a square grid, spaced apart by a uniform amount in each direction. This is shown by $D_y$ in the y-direction and $D_x$ in the x-direction. In general, the dots are spaced so that, collectively, they provide sufficient contrast reduction in the viewer's periphery for myopia reduction. Typically, smaller dot spacing will result in greater contrast reduction (provided adjacent dots do not overlap or merge). In general, $D_x$ and $D_y$ are in a range from about 0.05 mm (e.g., about 0.1 mm or more, about 0.15 mm or more, about 0.2 mm or more, about 0.25 mm or more, about 0.3 mm or more, about 0.35 mm or more, about 0.4 mm or more, about 0.45 mm or more, about 0.5 mm or more, about 0.55 mm or more, about 0.6 mm or more, about 0.65 mm or more, about 0.7 mm or more, about 0.75 mm or more) to about 2 mm (e.g., about 1.9 mm or less, about 1.8 mm or less, about 1.7 mm or less, about 1.6 mm or less, about 1.5 mm or less, about 1.4 mm or less, about 1.3 mm or less, about 1.2 mm or less, about 1.1 mm or less, about 1 mm or less, about 0.9 mm or less, about 0.8 mm or less). As an example, dot spacing can be 0.55 mm, 0.365 mm, or 0.240 mm.

While the protuberances shown in FIG. 1B are arranged with equal spacing in the x- and y-directions, more generally spacing in each direction may be different. Furthermore, protuberances may be arrayed in grids that are not square. For example, hexagonal grids may be used. Non-regular arrays are also possible, e.g., random or semi-random dot placement may be used. In the case of a random pattern dimensions given would be the average separation of the dots in X and Y directions.

While the dots are depicted as have circular footprints in FIG. 1B, more generally the dots can have other shapes. For example, the dots can be elongated in one direction (e.g., in the x-direction or y-direction), such as in the case of elliptical dots. In some embodiments, the dots are random on shape.

It is believed that light from a scene that is incident on the lenses in reduced contrast areas 130a and 130b between the dots contributes to an image of the scene on the user's retina, while light from the scene incident on the dots does not. Moreover, the light incident on the dots is still transmitted to the retina, so has the effect of reducing image contrast without substantially reducing light intensity at the retina. Accordingly, it is believed that the amount of contrast reduction in the user's peripheral field of view is correlated to (e.g., is approximately proportional to) the proportion of the surface area of the reduced-contrast areas covered by the dots. Generally, dots occupy at least 10% (e.g., 20% or more, 30% or more, 40% or more, 50% or more, such as 90% or less, 80% or less, 70% or less, 60% or less) of the area (as measured in the x-y plane) of reduced contrast area 130a and 130b.

In general, the dot pattern reduces the contrast of images of objects in the wearer's peripheral vision without significantly degrading the viewer's visual acuity in this region. Here, peripheral vision refers to the field of vision outside of the field of the clear aperture. Image contrast in these regions can be reduced by 40% or more (e.g., 45% or more, 50% or more, 60% or more, 70% or, more, 80% or more) relative to an image contrast viewed using the clear aperture of the lens as determined. Contrast reduction may be set according to the needs of each individual case. It is believed that a typical contrast reduction would be in a range from about 50% to 55%. Contrast reductions of lower than 50% may be used for very mild cases, while subjects who are more predisposed might need a higher than 55% contrast reduction. Peripheral visual acuity can be corrected to 20/30 or better (e.g., 20/25 or better, 20/20 or better) as determined by subjective refraction, while still achieving meaningful contrast reduction.

Contrast, here, refers to the difference in luminance between two objects within the same field of view. Accordingly, contrast reduction refers to a change in this difference.

Contrast and contrast reduction may be measured in a variety of ways. In some embodiments, contrast can be measured based on a brightness difference between different portions of a standard pattern, such as a checkerboard of black and white squares, obtained through the clear aperture and dot pattern of the lens under controlled conditions.

Alternatively, or additionally, contrast reduction may be determined based on the optical transfer function (OTF) of the lens (see, e.g., http://www.montana.edu/jshaw/documents/18%20EELE582_S15_OTFMTF.pdf). For an OTF, contrast is specified for transmission of stimuli in which light and dark regions are sinusoidally modulated at different "spatial frequencies." These stimuli look like alternating light and dark bars with the spacing between bars varying over a range. For all optical systems the transmission of contrast is lowest for the sinusoidally varying stimuli having the highest spatial frequencies. The relationship describing the transmission of contrast for all spatial frequencies is the OTF. The OTF can be obtained by taking the Fourier transform of the point spread function. The point spread function can be obtained by imaging a point source of light through the lens on to a detector array and determining how light from a point is distributed across the detector.

In the event of conflicting measurements, the OTF is technique is preferred.

In some embodiments, contrast may be estimated based on the ratio of the area of the lens covered by dots compared to the area of the clear aperture. In this approximation, it is assumed that all the light that hits the dots becomes uniformly dispersed across the entire retinal area, which reduce the amount of light available in lighter areas of an image and this adds light to darker areas. Accordingly, contrast reduction may be calculated based on light transmission measurements made through the clear aperture and dot pattern of a lens Generally, ophthalmic lenses 110a and 110b can be clear or tinted. That is, the lenses may be optically transparent to all visible wavelengths, appearing clear and/or colorless, or may include a spectral filter, appearing colored.

For example, ophthalmic lenses may include a filter that reduces the amount of red light transmitted to the wearer. It is believed that excessive stimulation of L cones in a person's eye (especially in children), may result in non-optimal eye lengthening and myopia. Accordingly, spectrally filtering red light using the ophthalmic lenses may further reduce myopia in a wearer.

Spectral filtering may be provided by applying a film to a surface of the lenses. Films may be applied by physically depositing material onto a lens surface, coating a layer of material on the surface, or laminating a preformed film onto the surface. Suitable materials include absorptive filter materials (e.g., dyes) or multilayer films, providing interference filtering. In some embodiments, spectral filtering may be provided by including a filtering material in the lens material itself and/or including a filtering material in the material used to form the protuberance.

Figure 2:
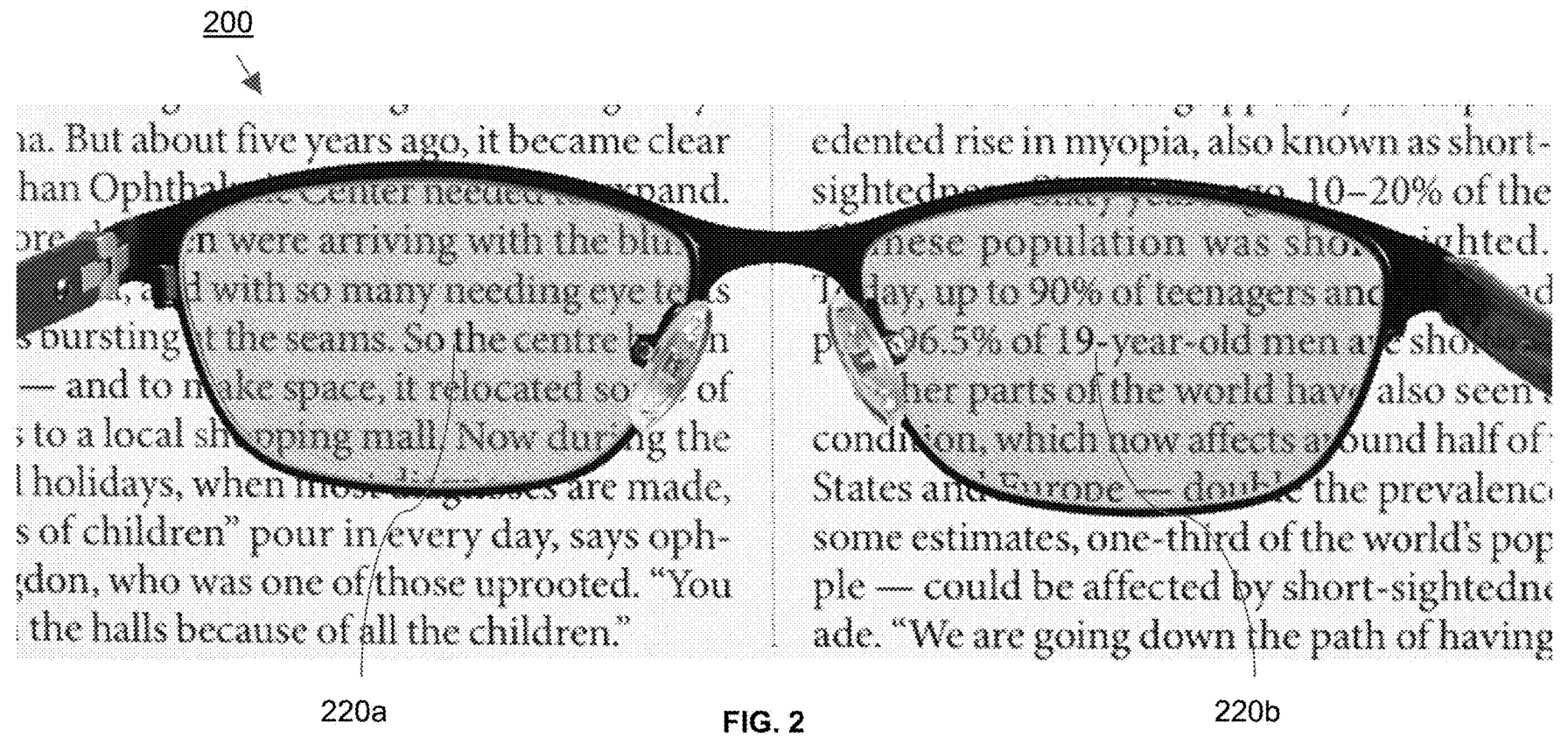

Referring to FIG. 2, the effect of spectral filtering and contrast reduction from the dot pattern is shown by viewing black text on a white background using eyeglasses 210. The white background to the text takes on a green appearance due to the filtering of red wavelengths from by the eyeglasses. Image contrast is unaffected at clear apertures 220a and 220b, but is reduced elsewhere in the viewer's visual frame.

Figure 3A:
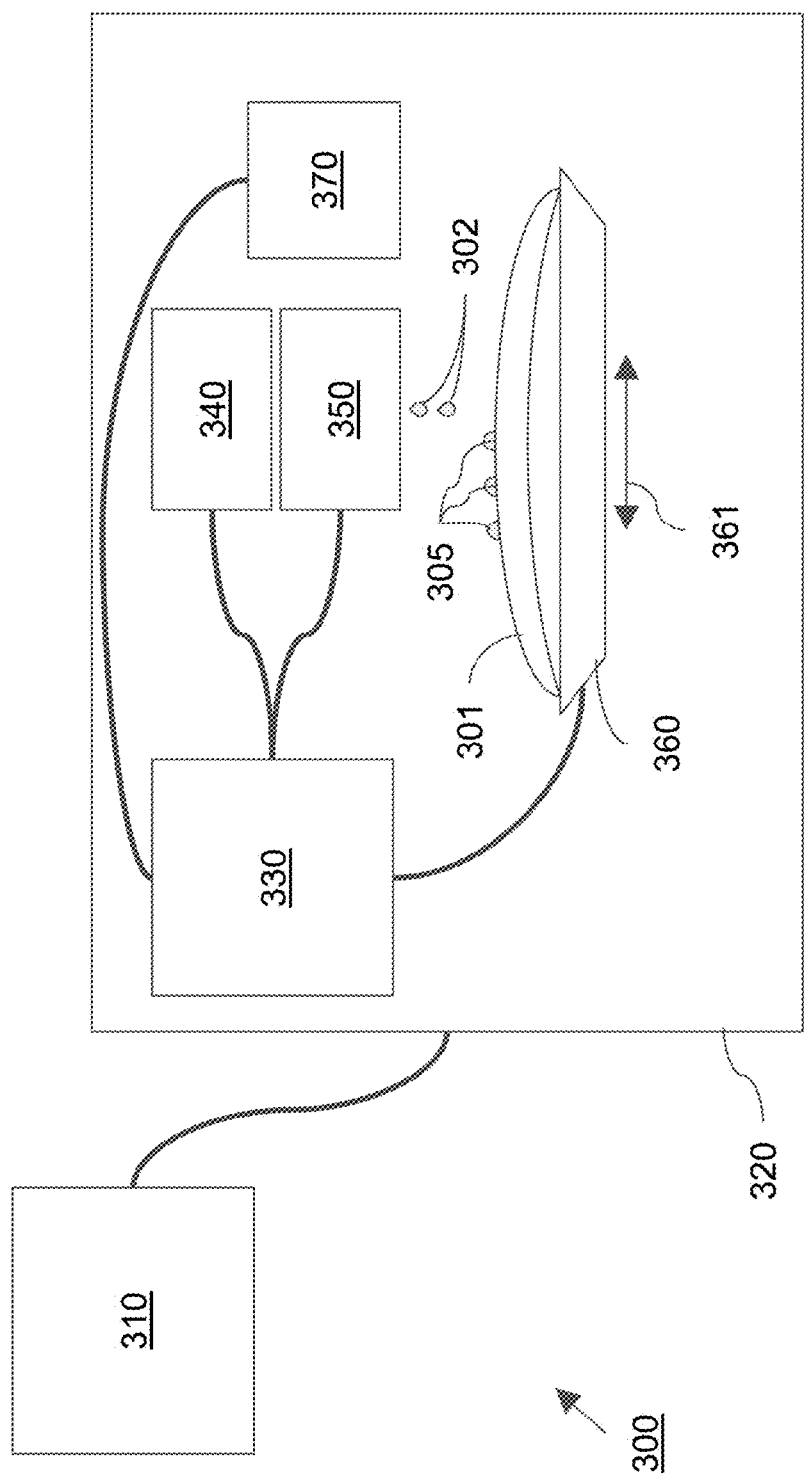
FIG. 3A shows an inkjet printing system for forming dot patterns on ophthalmic lenses.

In general, dots can be formed from lenses in a variety of ways including UV LED Direct-to-Substrate Printing, pad printing, hot stamping and screen printing technologies. In some embodiments, dots are formed by inkjetting a curable material onto a surface of a blank ophthalmic lens and then curing the material to set the dot pattern. Referring to FIG. 3A, an inkjetting and curing system 300 includes an inkjet printer 320 and a computer 310 in communication with the printer. Printer 320 includes a controller 330, a reservoir 340, an inkjet printhead 350, and a stage 360. Stage 360 supports a lens 301 and positions the lens relative to printhead 350. Reservoir 340 stores uncured material for inkjetting. Examples of curable material suitable for inkjetting includes various commercially-available proprietary monomers and oligomers that are cross-linked together, by photopolymerisation.

During operation, printhead 350 receives uncured material from reservoir 340.

Stage 360 moves lens 301 relative to printhead 350 (as depicted by arrows 361) while printhead 350 ejects drops of uncured material 302 toward the lens. Either the stage and/or printhead may be the moving part during this process. Drop volume varies depending on the desired protuberance dimensions. Drop volumes may be in a range from 0.001 $mm^3$ to 0.015 $mm^3$ (e.g., about 0.002 $mm^3$, about 0.003 $mm^3$, about 0.004 $mm^3$, about 0.005 $mm^3$, about 0.006 $mm^3$, about 0.008 $mm^3$, about 0.010 $mm^3$, about 0.012 $mm^3$). Upon contact with the lens surface, the drops wet the surface forming uncured protuberances 305. Alternatively, in some embodiments, stage 360 remains stationary while actuators move the printhead relative to the lens.

System 300 also includes a UV lamp 370. Stage 360 positions the lens adjacent lamp 370 so that the lamp can cure the deposited material, forming the final protuberances. Examples of suitable UV lamps include LEDs emitting in the wavelength range of 360-390 nm.

Controller 330 is in communication with reservoir 340, printhead 350, stage 360, and UV lamp 370 and coordinates the operation of each to facilitate printing and curing of the drops. Specifically, controller 330 controls the relative motion between printhead 350 and stage 360, the inkjet drop ejection frequency, and drop volume so that system 300 forms the desired dot pattern on lens 301. Controller 330 may also control the temperature of the uncured material (e.g., by a heater associated with reservoir 340 or elsewhere) to control the viscosity of the uncured material. The user inputs the drop pattern via computer 310, which generates corresponding control signals for the printer and communicates the signals to controller 330.

Commercially-available inkjet printers may be used. Suitable inkjet printers include Roland DGA (Irvine, Calif.) and Mimaki (Suwanee, Ga.) brands of UV LED Direct-to-Substrate Printers.

Figure 3B:
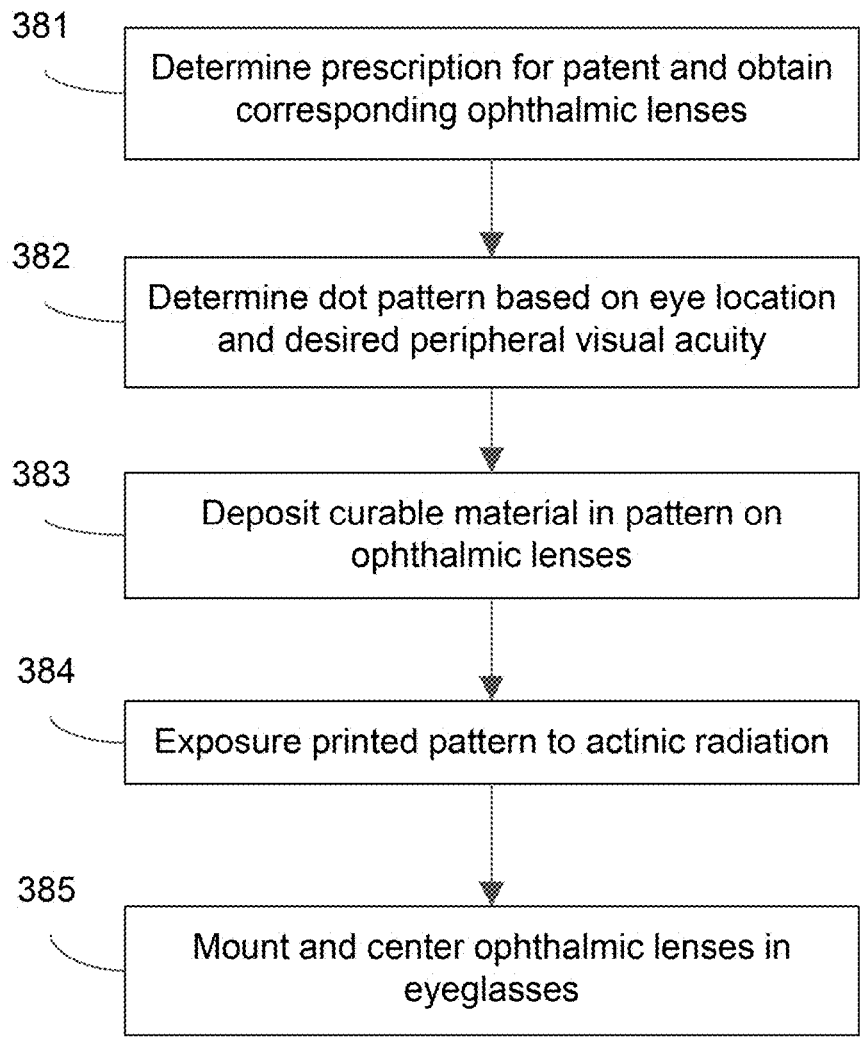
FIG. 3B is a flowchart showing steps in a method for making dot patterns using the system shown in FIG. 3A.

Inkjetting dot patterns allows an eye care professional to personalize dot patterns for a patient in an inexpensive and efficient manner. Referring to FIG. 3B, personalized eyeglasses are provided by a sequence 380 that may be performed entirely at the eye care professional's office. In a first step 381, the eye care professional determines the patient's prescription, e.g., by refracting the subject. This step determines the power of the ophthalmic lens upon which the dot pattern is formed. The patient also chooses their eyeglass frames in the same way they would for regular prescription glasses.

Figure 3C:
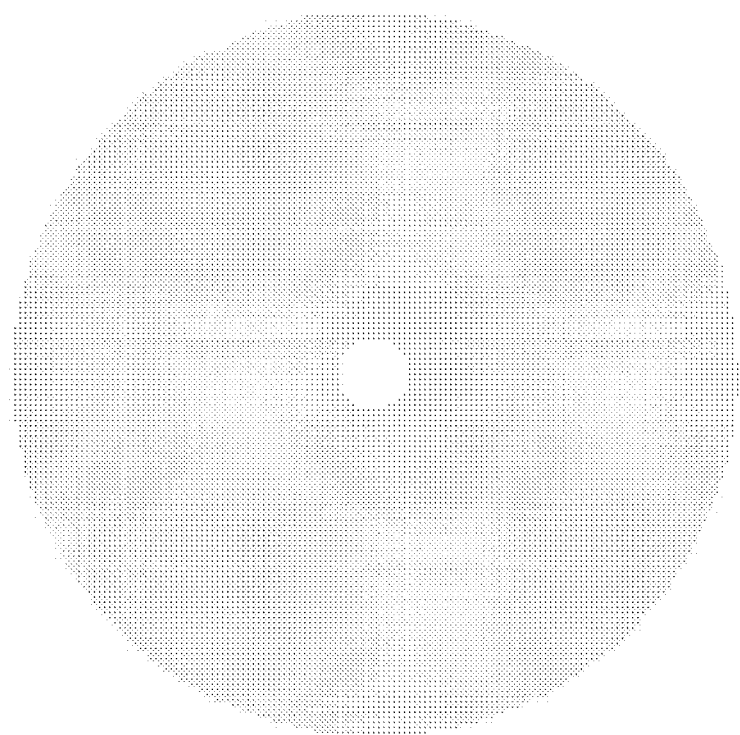
FIG. 3C shows a printing template for forming a dot pattern using the inkjet printing method of FIG. 3B.

In the next step 382, the eye care professional selects a dot pattern suitable for the patient. Parameters for the dot pattern that can be varied include, for example, dot size, dot density, clear aperture size and shape, and location of the clear aperture on the lens. Each of these may be individualized depending on the desired amount of contrast reduction in the peripheral vision and clear aperture angular range. An exemplary dot pattern is shown in FIG. 3C. This pattern prints dots over an area larger than most lens blanks, ensuring complete coverage of the lens surface by the dot pattern. Commercial software suitable for generating images (e.g., Microsoft Office products such as Visio, PowerPoint, or Word) may be used in conjunction with standard inkjet driver software to generate control signals for the inkjet printer. Alternatively, custom software can be used by the eye care professional to input the chosen parameters for the pattern into the ink jet printer's computer.

Next, in step 383, the ink jet printer deposits drops of uncured material in accordance with signals from the computer to form dots in the desired pattern. In step 384, the printed pattern is then exposed to curing radiation. In some embodiments, the center of the dot pattern, such as the clear center, is aligned to the optical center of the lens. This can be achieved, for example, by measuring and marking the optical center using a lensometer and aligning the print pattern with the marked optical center. In certain implementations, the optical center of the lens is first marked, then edged in a circular shape, such that the optical center is aligned to the geometric center of the circular lens. Drops are then printed on the lens so that the dot pattern is centered on the circular lens, which now corresponds to the optical center. Alternatively, or additionally, lens blanks can be made or chosen such that the optical center always matches the geometric center of the lens.

Finally, in step 385, the lenses are edged and mounted in the frames.

In some implementations, the lenses can be mounted in the frames and the frames fit to the wearer before the dots are cured. In this way, the printed dot pattern can be cleaned off the lens and the reprinted if necessary.

Figure 3D:
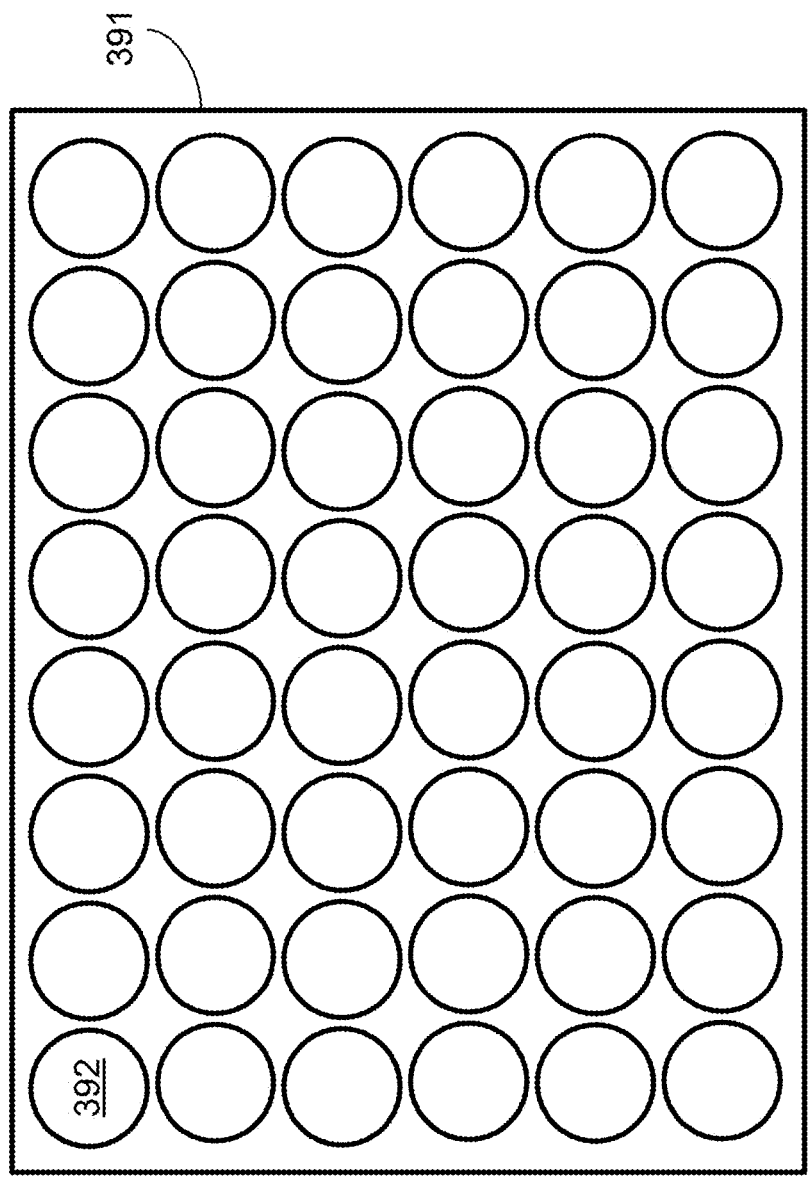
FIG. 3D shows a top view of a jig used for positioning multiple lenses in an inkjet printing system.

Referring to FIG. 3D, in some implementations, a jig 390 is used to support multiple lens blanks during lens manufacturing. Jig 390 includes a tray 391 that features an array of lens holders 392 on one surface, each sized to securely hold a lens. For example, if 60 mm diameter lens blanks are used, the lens holders each have a diameter of 60 mm to tightly hold a respective lens. During operation, jig 390 including one or more lenses is positioned on stage 360. The jig holds each lens in precise location so that system 300 can accurately jet onto the lenses' surface. In addition, the jig allows for manufacturing multiple lenses per batch. While the jig in FIG. 3D includes 48 lens holders, generally, jigs can be designed to hold any number of lenses subject to the physical constraints imposed by the ink jetting system. Many sizes of jigs are possible, for example jigs that accommodate about 24 lenses, about 48 lenses, about 100 lenses, about 200 lenses, about 300 lenses, about 400 lenses, about 500 lenses, or more than 500 lenses per run.

FIGS. 4A-4C show photographs of a lens printed using the pattern of FIG. 3C. FIG. 4A shows the entire lens, while FIGS. 4B and 4C show an enlarged portion of the dot pattern, the portion in FIG. 4C including the clear aperture.

Other methods for forming protrusions are also possible. For example, transfer or lithographic printing can be used instead of inkjetting. Transfer printing involves forming the protrusions on a different substrate and then transferring them to the surface of the lens in a separate process step. Lithographic printing may involve forming a continuous, uniform layer of the protrusion material on the lens surface and then patterning that layer to form the dot pattern. Optical or contact lithography can be used to pattern the layer. Alternatively, the protrusions can be molded on the lens surface using the same molding process used to form the lens. In this case, the protrusions are part of the lens mold. In some embodiments, the dot pattern may be provided by a film that is laminated onto a surface of the lens.

While the dot pattern in the embodiments described above are protrusions formed on a surface of the ophthalmic lens, other implementations that provide comparable optical properties and lens durability are also possible. For example, in some embodiments, contrast reduction is provided by arrays of recesses in a lens surface. The recesses can have dimensions similar to those of the protuberances described above. Recesses can be formed using a variety of techniques, such as etching (e.g., physical etching or chemical etching) or ablating material from the lens surface (e.g., using laser radiation or a molecular or ion beam). In some embodiments, recesses are formed when molding the lens.

Alternatively, or additionally, dot patterns can be embedded in the lens material itself. For example, transparent beads of appropriate size can be dispersed in the lens material when the lens is molded, where the refractive index of the bead material and bulk lens material differ. The clear aperture is formed from bulk lens material only.

In some embodiments, contrast reduction is produced by other diffusing structures, such as a roughened surface. Holographic diffusers or ground glass diffusers may be used. In some embodiments, a diffuser may be provided by a film that is laminated onto a surface of the lens.

While the foregoing description pertains to ophthalmic lenses for eyeglasses, the principles disclosed may be applied to other forms of ophthalmic lenses, such as contact lenses. In some embodiments, dot patterns may be provided on contact lenses to provide similar therapeutic effects. The size and spacing of dots in a contact lens dot pattern may be sized so that they subtend comparable solid angles in a user's visual field to the dot patterns described for eyeglass lenses above.

Dot patterns may be formed on contact lenses in a variety of ways. For example, dot patterns may be printed or transferred to a contact lens surface using the techniques described above. Alternatively, the dot patterns may be formed by dispersing scattering materials in the contact lens.

In some embodiments, dots are formed on one or both surfaces of a contact lens by exposing a contact lens surface to laser radiation. The laser radiation locally ablates the contact lens material at the surface, leaving a small depression. By selectively exposing the contact lens surface to laser radiation, a dot pattern can be formed on the surface. For example, the laser's beam can be moved relative to the surface while the beam is pulsed. Relative motion between the beam and the contact lens surface can be caused by moving the beam while leaving the surface fixed, moving the surface while leaving the beam fixed, or moving both the beam and the surface.

Referring to FIG. 13, a laser system 1300 for forming dots on a surface of a lens includes a laser 1320, a beam chopper 1330, focusing optics 1340, a mirror 1350, and a stage 1370. Laser 1320 directs a laser beam towards mirror 1350, which deflects the beam towards a contact lens 1301 which is positioned relative to the mirror 1350 by stage 1370. An actuator 1360 (e.g., a piezoelectric actuator) is attached to mirror 1350. The stage includes a curved mounting surface 1380 which supports contact lens 1301. Laser system 1300 also includes a controller (e.g., a computer controller) in communication with laser 1320, beam chopper 1330, and actuator 1360.

Beam chopper 1330 and focusing optics 1340 are positioned in the beam path. Chopper 1330 periodically blocks the beam so that contact lens 1301 is exposed to discrete pulses of laser light. Focusing optics 1340, which generally includes one or more optically powered elements (e.g., one or more lenses), focuses the beam to a sufficiently small spot on the surface of contact lens 1301 so that the area ablated by the beam on the lens surface corresponds to the desired dot size. Actuator 1360 changes the orientation of mirror 1350 with respect to the beam to scan the pulsed beam to different target points on the contact lens surface. Controller 1310 coordinates the operation of laser 1320, chopper 1330, and actuator 1360 so that the laser system form a predetermined dot pattern on the contact lens.

In some implementations, stage 1370 also includes an actuator. The stage actuator can be a multi-axis actuator, e.g., moving the contact lens in two lateral dimensions orthogonal to the beam propagation direction. Alternatively, or additionally, the actuator can move the stage along the beam direction. Moving the stage along the beam direction can be used to maintain the exposed portion of the lens surface at the focal position of the beam, notwithstanding the curvature of the lens surface, thereby maintaining a substantially constant dot size across the lens surface. The stage actuator can also be controlled by controller 1310, which coordinates this stage motion with the other elements of the system. In some embodiments, a stage actuator is used in place of the mirror actuator.

Generally, laser 1320 can be any type of laser capable of generating light with sufficient energy to ablate the contact lens material. Gas lasers, chemical lasers, dye lasers, solid state lasers, and semiconductor lasers can be used. In some embodiments, infrared lasers, such as a $CO_2$ laser (having an emission wavelength at 9.4 µm or 10.6 µm) can be used. Commercially-available laser systems can be used such as, for example, $CO_2$ laser systems made by Universal Laser Systems, Inc. (Scottsdale, Ariz.), (e.g., the 60 W VLS 4.60 system).

Figure 14B:
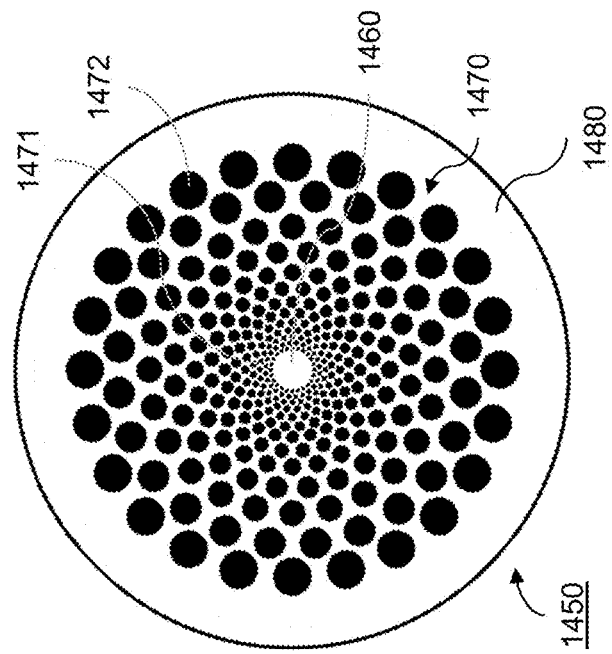
FIGS. 14A-B are examples of dot patterns for contact lenses.
Figure 14A:
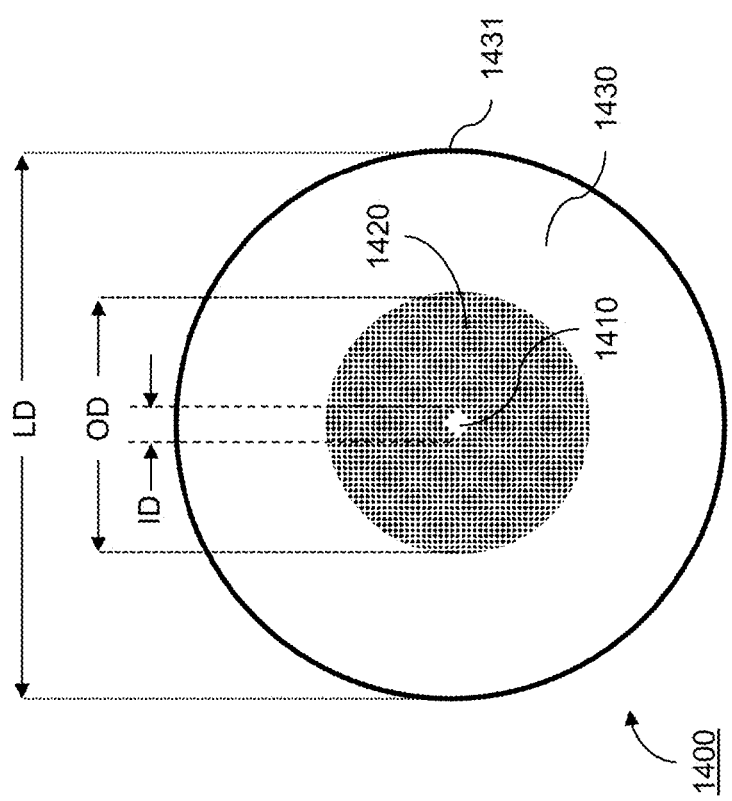

The pulse duration and pulse energy are typically selected to ablate an amount of material from the contact lens surface to provide a dot of a desired size. An example dot pattern for a contact lens is shown in FIG. 14A. Here, contact lens 1400 includes a clear aperture 1410, a reduced-contrast region 1420, and a clear outer region 1430. Reduced-contrast region 1420 is an annular region having an inner diameter ID and an outer diameter OD. ID corresponds to the diameter of clear aperture 1410. The contact lens has a lens diameter, LD, which is greater than OD.

Typically, ID is less than the user's pupil diameter under normal indoor lighting conditions (e.g., such as typical classroom or office lighting in which a user is able to easily read text from a book). This ensures that, under such lighting conditions, image contrast in the user's peripheral visual field is reduced. In some embodiments, ID is in a range from about 0.5 mm to about 2 mm (e.g., in a range from about 0.75 mm to about 1.75 mm, in a range from about 0.9 mm to about 1.2 mm, about 0.6 mm or more, about 0.7 mm or more, about 0.8 mm or more, about 0.9 mm or more, about 1 mm or more, about 1.1 mm or more, about 1.2 mm or more, about 1.9 mm or less, about 1.8 mm or less, about 1.7 mm or less, about 1.6 mm or less, about 1.5 mm or less, about 1.4 mm or less, about 1.3 mm or less).

Generally, OD is sufficiently large so that the reduced-contrast region extends beyond the user's pupil under normal indoor lighting conditions. In some embodiments, OD is about 2.5 mm or more (e.g., about 3 mm or more, about 4 mm or more, about 5 mm or more, such as about 10 mm or less, about 8 mm or less, about 7 mm or less, about 6 mm or less).

Generally, the dimensions and spacing between the dots in the contact lenses are selected so as to provide the desired optical effect (e.g., as described above), subject to the constraints of the method used to form the dots. In some embodiments, the dots can have a maximum lateral dimension in a range from about 0.005 mm or more (e.g., about 0.01 mm or more, about 0.015 mm or more, about 0.02 mm or more, about 0.025 mm or more, about 0.03 mm or more, about 0.035 mm or more, about 0.04 mm or more, about 0.045 mm or more, about 0.05 mm or more, about 0.055 mm or more, about 0.06 mm or more, about 0.07 mm or more, about 0.08 mm or more, about 0.09 mm or more, about 0.1 mm) to about 0.5 mm or less (e.g., about 0.4 mm or less, about 0.3 mm or less, about 0.2 mm or less, about 0.1 mm).

The spacing of the dots can also vary so as to provide the desired optical effect. Typically, the spacing of the depressions (i.e., as measured between the center of adjacent depressions) are in a range from about 0.05 mm (e.g., about 0.1 mm or more, about 0.15 mm or more, about 0.2 mm or more, about 0.25 mm or more, about 0.3 mm or more, about 0.35 mm or more, about 0.4 mm or more, about 0.45 mm or more) to about 1 mm (e.g., about 0.9 mm or less, about 0.8 mm or less, about 0.7 mm or less, about 0.6 mm or less, about 0.5 mm or less).

The relative area of dots in the reduced-contrast region can vary as described above for eyeglass lenses.

LD corresponds to the diameter of the contact lens and is typically in a range from about 10-20 mm. Generally, LD is greater than OD by at least 1 mm or more (e.g., about 2 mm or more, about 3 mm or more, about 4 mm or more, about 5 mm or more, about 6 mm or more, about 7 mm or more, such about 8 mm). Including at least some space at the edge of the contact lens that does not include dots ensures that the dots do not reduce the integrity of the contact lens at its edge (e.g., by tearing) or reducing the integrity of the seal between the contact lens and the user's eyeball.

While the contact lens dot pattern shown in FIG. 14A features dots that each have the same size and the same spacing between adjacent dots, other dot arrangements are possible. For example, referring to FIG. 14B, a contact lens 1450 features dots having varying sizes. Here, contact lens 1450 includes a clear aperture 1460, a reduced-contrast region 1470, and a clear outer region 1480. Reduced-contrast region 1470 includes a dot pattern in which the size of the dots increases as the radial distance of the dot position with respect to the center of the lens increases. Accordingly, dots 1471 closest to clear aperture 1460 are the smallest, while dots 1472 closest to outer region 1480 are the largest.

Although system 1300 is shown as ablating a contact lens, more generally, laser ablation can be used for eyeglass lenses too.

While myopia progression and treatment efficacy may be monitored in subjects using a variety of techniques (e.g., including subjective refraction and/or eye length measurements), it is believed that changes in choroidal thickness (i.e., an increase in the choroidal thickness) is a reliable biomarker for this purpose. Choroid thickness can be measured using optical coherence tomography (OCT). Exemplary deep field OCT images showing the choroid thickness in a subject are shown in FIGS. 5A and 5B. The choroid, shown in cross-section between the two yellow curves spanning the image field from left to right. Because OCT images may have variable magnification, an internal landmark that doesn't change thickness over the course of treatment may be used as a reference when making thickness measurements. An example of such a landmark is the retinal pigmented epithelium (RPE) layers between the choroid and the retina, whose thickness is indicated by the red line shown in FIG. 5B.

EXAMPLES

Initial Study/Comparative Example

In prior investigations, it was found that proof-of-concept eyeglasses using diffusing filters attached to the surface of the lenses could slow axial length growth in subjects but there were a number of challenges. The filter used was a commercially available Bangerter Occlusion Foil ("BOF"). These were diffusers made of thin flexible static vinyl film which was trimmed to match the lens shape and adhered to the right lens. The "foil" used was "BOF-0.8 Acuity of 20/25" which, as the name implies, nominally reduced best corrected acuity to 20/25. However, in practice, acuity of subjects who could be best corrected in the range of 20/15-20/20, tested in the range 20/30-20/40 with the BOF-0.8 filter in place. The subjects of this study wore the diffuser unilaterally on one eye was because of the large reduction in acuity it produced and there was concern about the tolerability and safety of wearing spectacles that reduced acuity to 20/30-40 binocularly. By making the diffuser arm monocular, subjects of this study were able to function normally because they had one eye they could use for high acuity vision. However, ideally, in a commercial product, the treatment should be done to both eyes simultaneously.

Another problem with the Initial Study was that the vinyl filters could detach from the lenses accidentally. In order to deal with this problem, in the trial, each subject was provided with two pairs of glasses with the instruction to use the second pair if the filter came off the first pair. Then, it was possible to supply the subject with a new backup pair. Ideally, in a commercial product the diffuser should be a durable as standard lenses.

New Study

Prototype lenses were designed to address problems with the spectacles used in the Initial Study and at the same time maintain or improve efficacy in slowing growth of axial length. It is believed that the main reason the BOF-0.8 filters reduced acuity so drastically was because of the very poor optical quality of the vinyl film itself. Non-uniformities in thickness produced a "wavy" pattern that distorted the image making vision difficult. However, it was believed this degradation of the image did not have any therapeutic value. Thus, one goal for the prototype lenses of the new study was to eliminate any kind of film applied to the eyeglasses and provide the diffuser as a permanent part of the lens itself. In the new design, the diffuser component of these lenses serves the purpose of lowering contrast of the image but every other aspect of the optical quality is substantially the same as the standard of care.

A first step in the development of the eyeglasses was to produce a lens that replicated the amount of diffusion (and presumably the therapeutic value) of the BOF-0.8 filter but had all the other optical properties of a standard (i.e., non-diffusing) lens. Efficacy of the new prototypes were compared with the BOF-0.8 filter of the Initial Study which was used as the standard for efficacy. In order to reduce the length of the study on new prototypes, choroid thickening measured using optical coherence tomography (OCT) was used as a biomarker for treatment efficacy. The choroid was imaged using OCT and it was demonstrated that the BOF-0.8 filter produced a thickening of the choroid that could be accurately measured. Images from this study are shown in FIGS. 6A-6D. OCT non-invasively provides a cross-sectional view of the retina through the fovea. Several layers can be resolved including the inner limiting membrane nerve fiber layer (NFL), ganglion cell layer (GCL), inner plexiform layer (IPL), inner nuclear layer (INL), junction between the inner and outer segment of the photoreceptors (IS/OS PR), outer nuclear layer (ONL), retinal pigment epithelium (RPE). The very deepest layer is the choroid. FIGS. 6A and 6C show the unsegmented images of the retina from one subject before and after treatment with the BOF-0.8 filter. A relative thickening of the choroid layer is evident post-treatment compared to pretreatment. FIGS. 6B and 6D include segment lines (in red) showing the outer bounds of the choroid. FIG. 6C shows the choroid at day 39 post-treatment. FIG. 6D shows the choroid at day 39 post-treatment with the outerbound of the choroid demarcated. Thickness was measured as the distance from the boundary line to the RPE boundary.

FIG. 7 shows a plot of relative choroid thickness as a function of location on the retina for this study. A marked post-treatment thickening (upper, blue curve) of the choroid is evident across the retina compared to the pre-treatment measurements (lower, black curve).

Example: Prototype I

A first prototype eyeglasses, prototype I, was developed to provide a lens that incorporated diffusive elements and lowered the contrast of the image substantially the same amount as the BOF-0.8 filter while being practical and durable and free of the many optical imperfections of the vinyl substrate of the BOF-0.8 filter. The lens for formed by inkjet printing a dot pattern on lenses using a UV-curable material. Printers from the Roland DG VersaUV line of inkjet printers and Mimaki UV flat bed printers were both used in different versions of prototype I. The UV-curable materials were also obtained from Roland and Mimaki.

Figure 8:
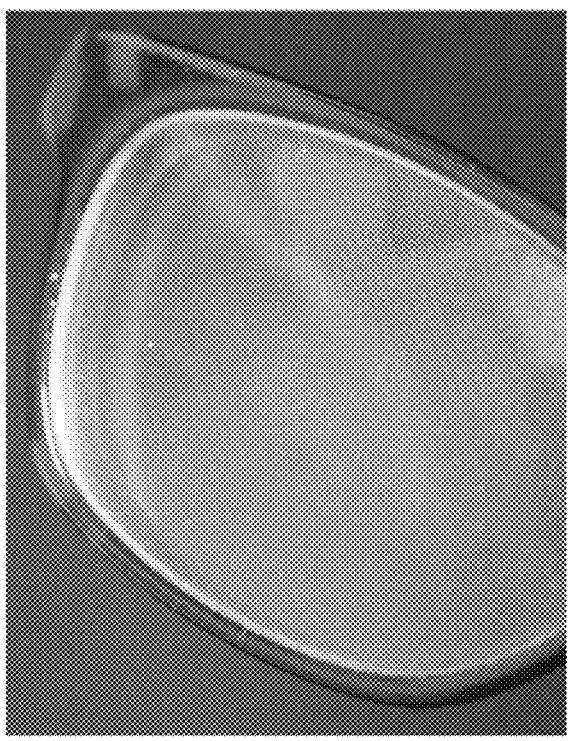
FIG. 8 is a photograph showing a dot pattern used in prototype I lenses.
Figure 11:
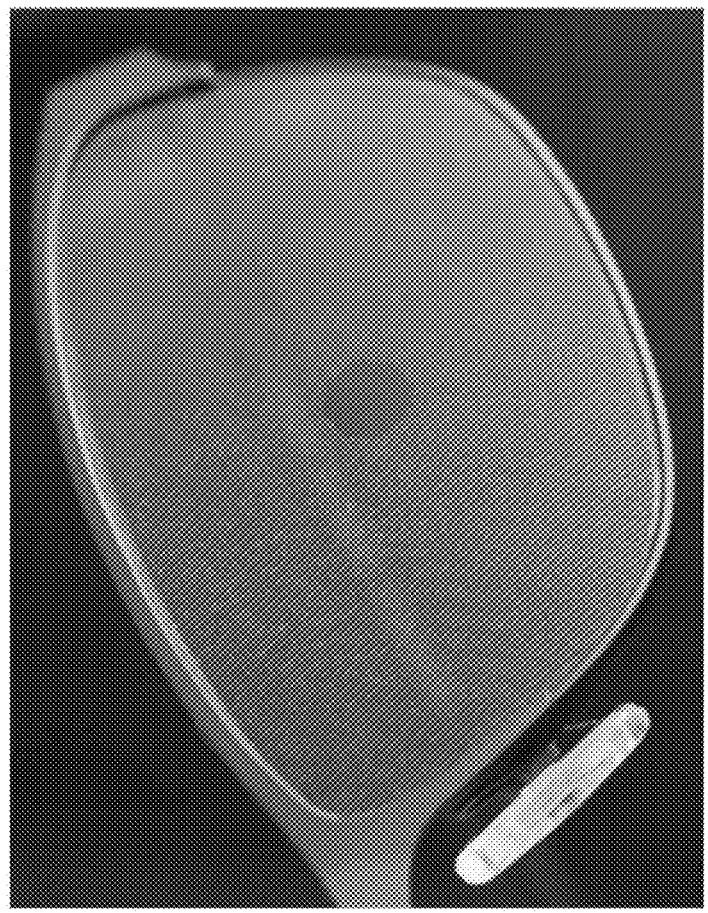
FIG. 11 is a photograph showing a dot pattern used in prototype III lenses.

The lenses were clear polycarbonate, shatterproof lenses, without any spectral filtering. The dot pattern was printed on a square grid having a spacing of 0.55 mm. The volume of each dot was 0.004 $mm^3$. The dot pattern covered the entire lens; no clear aperture remained. The printed pattern was cured using UV LEDs emitting in the range 365 nm-385 nm. A photograph of an example prototype I lens is shown in FIG. 8.

We tested prototype I lens using a within-subjects protocol. A small number of subjects were recruited and refracted to their best corrected visual acuity. The hypothesis that the initial reduction in axial length was the result of choroidal thickening was tested with an OCT study.

After a week of baseline measurements, subjects wore glasses with an untreated left eye (OS) lens and a BOF-0.8 filter attached to the right eye (OD) lens. After four weeks, subjects then switched to the new prototype lenses on their left eyes (OS) and the right eyes wore untreated lenses. The absolute difference between the choroid thickness of the left and right eyes (OD-OS) increased significantly after a month of BOF-0.8 filter wear over the right eye. When the OD glasses were removed and the OS eye was treated with prototype I there was a corresponding significant decrease in the axial length of OS (p=0.0083) and an increase in the OD-OS value (p=0.0032). There was no significant difference between the effectiveness of prototype I and the BOF-0.8 filter with respect to producing an increase in choroid thickness. However, there was a drastic difference in best corrected visual acuity when wearing our prototype I compared to the BOF-0.8 filter.

Example 2: Prototype II

Figure 9:
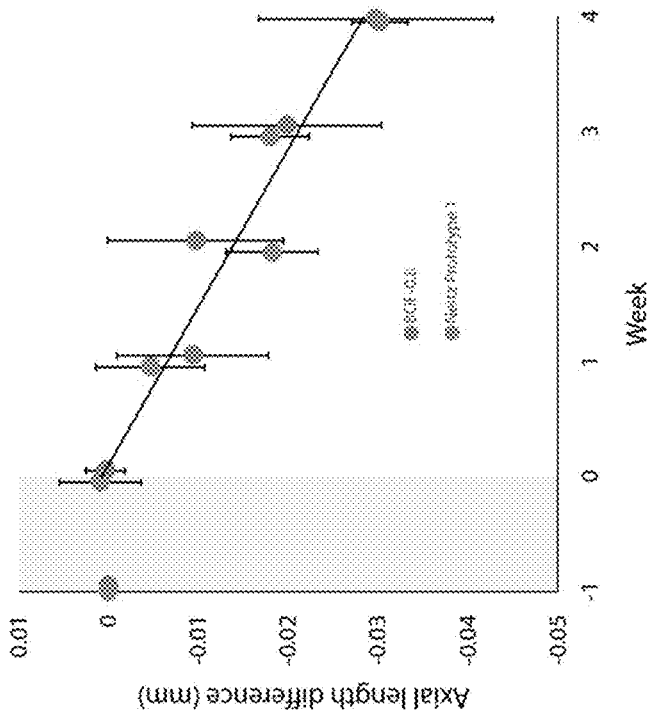
FIG. 9 is a plot comparing results of a study conducted using prototype I lenses and an Initial Study. The time progression of axial length difference measurements are plotted.

The goal for prototype II was to produce a lens that would allow measured best corrected visual acuities of 20/15-20/20 but have effectiveness as good or better than the BOF-0.8 filter. To this end, prototype II lenses were produced by modifying the prototype I dot pattern to incorporate a small central clear area. The dots were formed on a square grid pattern with a spacing of 0.55 mm. The clear aperture was formed in with a circular shape of diameter 3.8 mm. A photograph of a prototype II lens is shown in FIG. 9.

When the glasses were fitted, the clear area was positioned to match the pupil allowing the wearer to look through the clear area when viewing straight ahead. Subjects who were best corrected to 20/15-20/20 tested as 20/15-20/20 when wearing prototype II and reading the eye chart looking through the clear area.

We tested prototype II with the clear area against prototype I by recruiting a small number of subjects and having them wear the lens with the clear area on the left eye and the lens without on the right eye. We then compared increases in choroidal thickness between the two eyes and found no difference between the lenses with the clear area and the lens without. This demonstrated that it is possible to design a diffuser lens without spectral light filtering, that allowed subjects to test with best corrected acuities of 20/15-20/20 and still maintain the effectiveness (as measured by increases in choroid thickness) of the original lens used in the Initial Study.

Example 3: Prototype III

Figure 10:
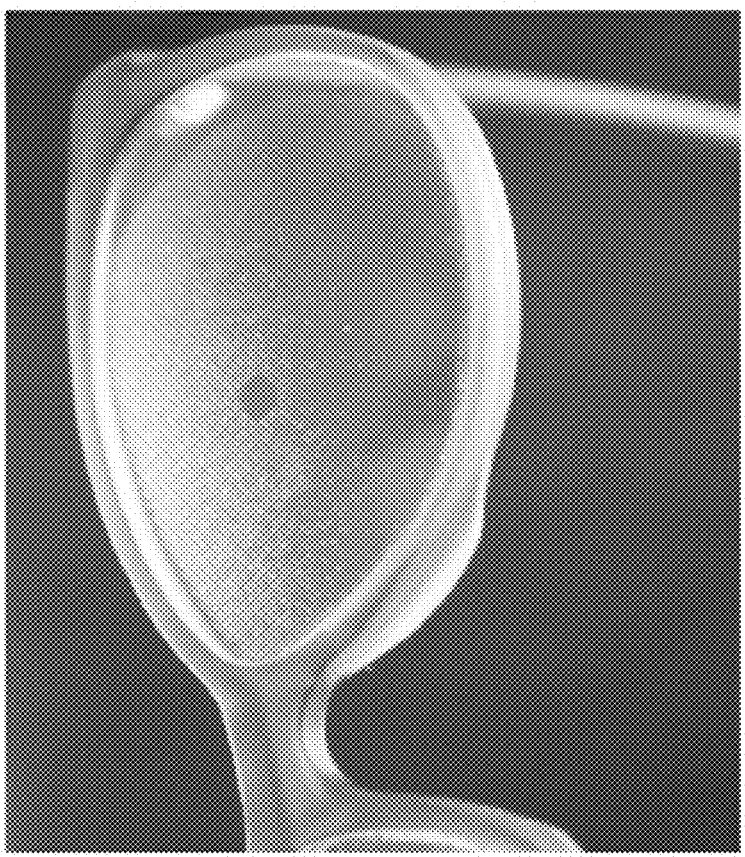
FIG. 10 is a photograph showing a dot pattern used in prototype II lenses.

Further improvements were explored to simultaneously maximize tolerability and effectiveness. We felt that the larger the clear area the more tolerable the prototype would be but also hypothesized that increasing the peripheral contrast reduction might increase the effectiveness. Thus, we experimented with these two variables producing another prototype: prototype III. Like prototypes I and II, prototype III did not have a spectral light filtering. The dot pattern for prototype III was modified to include a larger clear aperture and a greater reduction in contrast outside the clear area than prototype II. In particular, the clear aperture was enlarged to a 5.0 mm diameter and the square grid spacing reduced to 0.365 mm. Dot size remained the same as prototype II. A photograph of a prototype III lens is shown in FIG. 10.

A design goal was to develop a prototype that allows good vision that children and their parents are happy and comfortable with. Visual acuity with prototype III for children with best corrected acuity of 20/15-20/20 was 20/15-20/20 when vision was tested viewing through the clear aperture of the lens. We also tested acuity "off-axis" with the subject viewing through the peripheral diffuser. Subjects with best corrected acuity of 20/15-20/20 through the clear aperture demonstrated 20/20-20/25 vision when viewing through the diffusing area.

We initiated a small trial with the prototype III lens worn binocularly. The main objective of the lens was to assay durability and tolerability of the lens. The trial had one arm. Subjects were aged 7 to 10 years of age with a history of myopic progression. Subjects were all referred to us by ophthalmologists because parents were concerned about rapidly progressing myopia in their children. The study had a single site, which was ophthalmology research at the University of Washington in Seattle. 8 children were enrolled. Preliminary results for 4 children who passed 6 month wearing the glasses were obtained, monitoring axial length with an optical biometer, the IOLMaster from Carl Zeiss Meditec. Children were also asked to keep a journal documenting how many hours a day they wear the lenses and noting any problems or concerns they had with the eyeglasses.

When subjects came to the lab for axial length measurements, we viewed their journal and inspected the eyeglasses for any signs change or deterioration. We also asked the subjects and their parents if they had any problems or concerns with the eyeglasses. There were no noted problems with the durability of the eyeglasses and the subjects and parents had no complaints.

Figure 12:
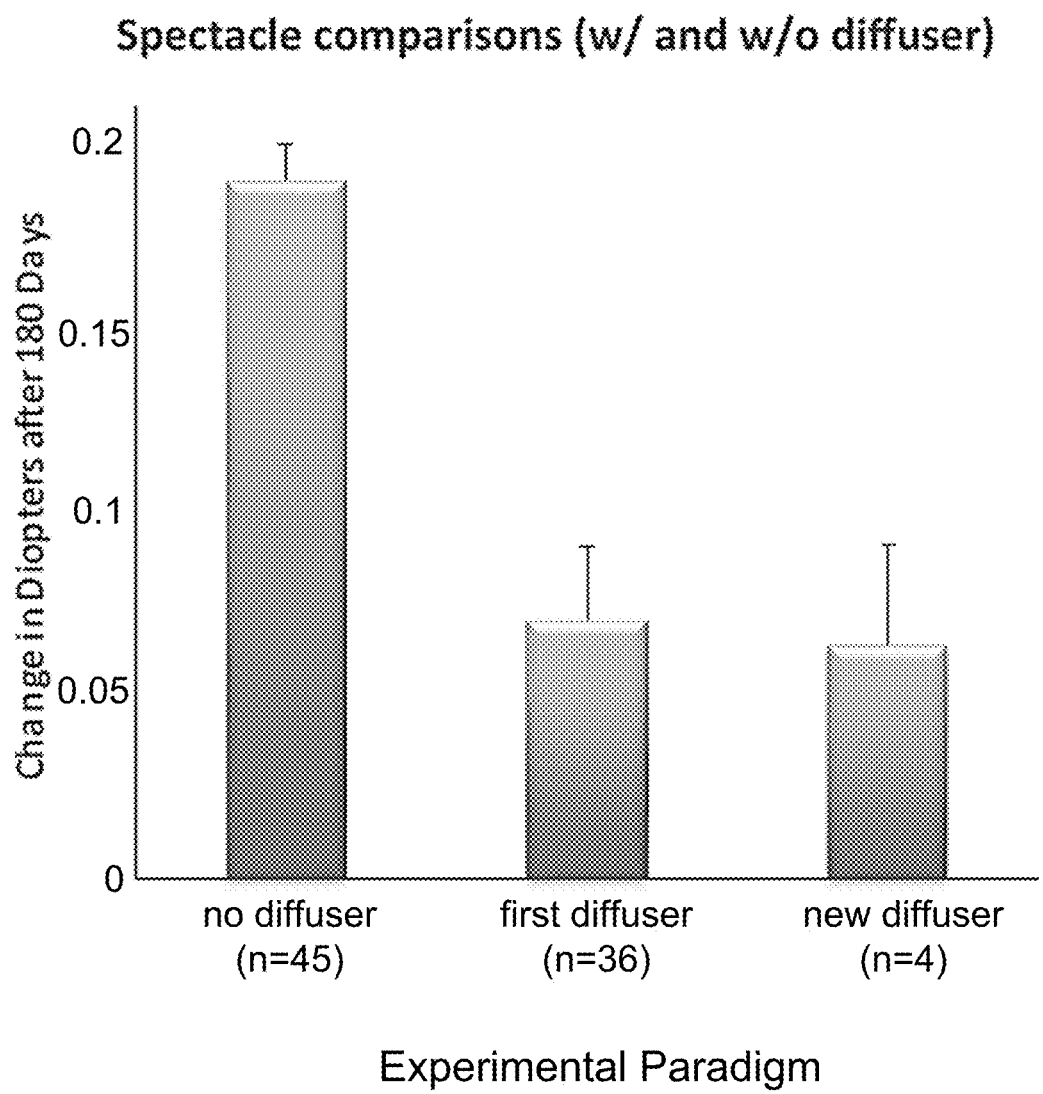
FIG. 12 is a bar chart comparing change in diopters after 180 days for subjects from the Initial Study ("first diffuser"), prototype III lenses ("new diffuser"), and a control group ("no diffuser").

However, referring to FIG. 12, it is interesting to compare axial growth the subjects wearing prototype III with the results of the Initial Study at 6 months. This figure shows a bar chart comparing the change in diopters after 180 days for subjects' eyes. The first bar represents the control eyeglasses and the second bar represents the original diffuser eyeglasses from the Initial Study. The third bar represents Prototype III after 6 months for the four children who completed 6 months in the study.

What we have demonstrated is that we are able to manufacture stable and durable spectacles that allow 20/15-20/20 vision. In this small group of subjects were very satisfied with the spectacles and they show a slow rate of progression after 6 months.

Example 4: Contact Lenses

Dot patterns were formed on contact lenses as follows. In each case, a −7.5 D contact lens was positioned on a ball bearing on the stage of a VLS 4.60 CO2 laser system (Universal Laser Systems, Inc., Scottsdale, Ariz.). The lens diameter in each case was 14 mm.

Contact lenses were exposed at 5% power, 10% power, and 20% power settings respectively. In each exposure, the laser scan speed was set to 25% and the resolution set to 0.002 inches. The exposure area had an outer diameter of 12.7 mm and an inner diameter of 1 mm. The exposure pattern within the area was a square grid with a grid spacing of 0.0116 inches.

A visible dot pattern was formed for 5% and 10% power settings. The 20% power setting resulting in cutting through the contact lens.

Figure 15B:
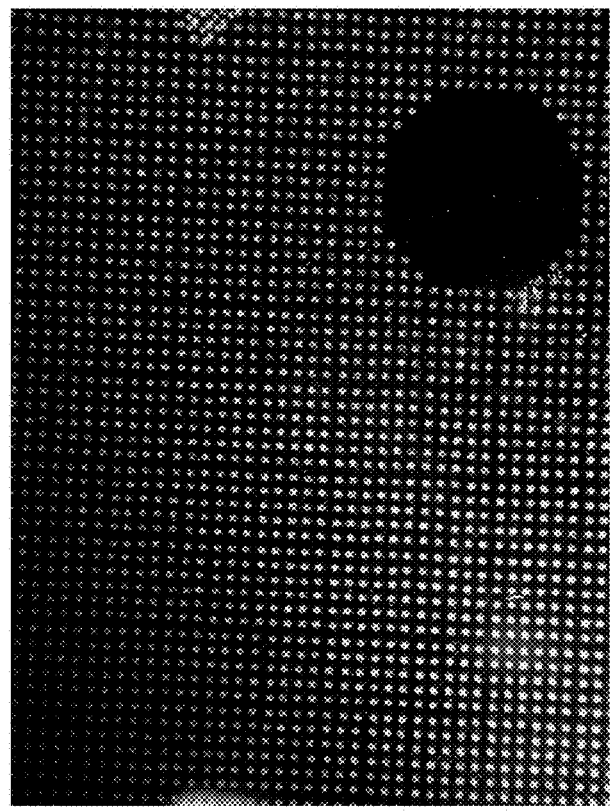
FIG. 15B is a photograph of an eyeglass lens with a dot pattern.
Figure 15A:
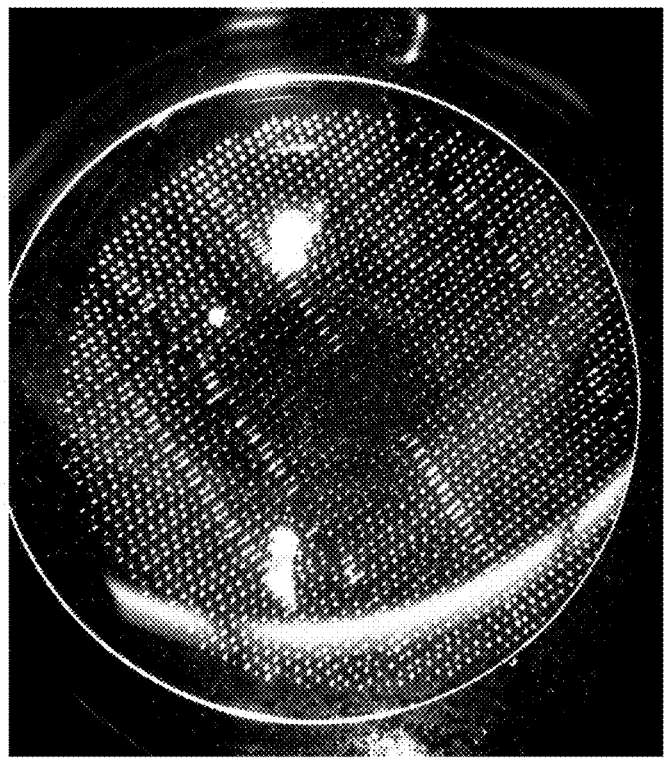
FIG. 15A is a photograph of a contact lens with a dot pattern.

A photograph of one of the contact lenses is shown in FIG. 15A. The dot pattern is clearly visible.

Example 5: Eyeglass Lenses Using Laser Ablation

Dot patterns were formed on several Trivex eyeglass lenses using a 60 W, 10.6 μm, VLS 4.60 CO2 laser system (Universal Laser Systems, Inc., Scottsdale, Ariz.). Lenses were exposed various powers between 5% and 40% and in both raster and vector print modes. The laser was set at 1,000 PPI. Speed settings were 25% or 100%.

A photograph of a lens exposed in vector mode is shown in FIG. 15B. The dot pattern in this example, which was printed in vector mode, is clearly visible.

A number of embodiments are described. Other embodiments are in the following claims.

What is claimed is:

1. An ophthalmic lens, comprising:
    a clear aperture;
    a region surrounding the clear aperture comprising a plurality of dots on a surface of the ophthalmic lens, each dot having a circular shape in a plane of the ophthalmic lens, each dot having a diameter of 0.08 mm or more;
    wherein, in a plane of the ophthalmic lens, a center of each dot in the region is arranged on one of a plurality of concentric circles surrounding the aperture, and
    wherein the dots are configured and positioned to reduce a contrast of an image viewed through the region compared with the image viewed through the clear aperture,
    wherein the ophthalmic lens is a spectacle lens.

2. The ophthalmic lens of claim 1, wherein the dots reduce the contrast of the image viewed through the region by a lensing effect.

3. The ophthalmic lens of claim 1, wherein the dots reduces the contrast by at least 30%.

4. The ophthalmic lens of claim 3, wherein the dots reduces the contrast by at least 50%.

5. The ophthalmic lens of claim 1, wherein the clear aperture is a circular aperture.

6. The ophthalmic lens of claim 5, wherein the circular aperture has a diameter of about 1 mm or more.

7. The ophthalmic lens of claim 1, wherein each of the dots on a corresponding one of the concentric circles has the same diameter.

8. The ophthalmic lens of claim 7, wherein dots on different ones of the concentric circles have different diameters.

9. The ophthalmic lens of claim 8, wherein the diameter of dots on different concentric circles increases with increasing radius of the concentric circles.

10. The ophthalmic lens of claim 1, wherein a spacing between adjacent dots is 0.5 mm or less.

11. The ophthalmic lens of claim 1, wherein the ophthalmic lens has optical power to correct a user's on-axis vision to 20/20 or better through the clear aperture.

12. The ophthalmic lens of claim 1, wherein the ophthalmic lens reduces the rate of myopia progression in a human subject.

13. The ophthalmic lens of claim 1, wherein each dot has a diameter of 1 mm or less.

14. The ophthalmic lens of claim 1, wherein each dot is a protuberance on the surface of the lens.

15. The ophthalmic lens of claim 1, wherein the dots occupy at least 10% of an area of the region.

* * * * *